US009382264B2

(12) United States Patent
Gessner et al.

(10) Patent No.: US 9,382,264 B2
(45) Date of Patent: Jul. 5, 2016

(54) CONVENIENTLY PREPARED NAPHTHALENE AND PERYLENE DERIVATIVES AS BUILDING BLOCKS FOR ORGANIC ELECTRONIC MATERIALS AND DYESTUFF

(71) Applicants: BASF SE, Ludwigshafen (DE); Max-Planck-Gesellschaft zur Foerderung der Wissenschaften e.V., Munich (DE)

(72) Inventors: Thomas Gessner, Heidelberg (DE); Helmut Reichelt, Neustadt (DE); Yulian Zagranyarski, Sofia (BG); Long Chen, Mainz (DE); Chen Li, Cologne (DE); Klaus Muellen, Cologne (DE)

(73) Assignees: BASF SE, Ludwigshafen (DE); MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 14/424,748

(22) PCT Filed: Aug. 27, 2013

(86) PCT No.: PCT/IB2013/058009
§ 371 (c)(1),
(2) Date: Feb. 27, 2015

(87) PCT Pub. No.: WO2014/033622
PCT Pub. Date: Mar. 6, 2014

(65) Prior Publication Data
US 2015/0225418 A1 Aug. 13, 2015

Related U.S. Application Data

(60) Provisional application No. 61/694,783, filed on Aug. 30, 2012.

(30) Foreign Application Priority Data

Aug. 30, 2012 (EP) ................................. 12182331

(51) Int. Cl.
| C07D 495/06 | (2006.01) |
| C07C 255/52 | (2006.01) |
| C07C 69/76 | (2006.01) |
| C07C 43/29 | (2006.01) |
| C07F 7/08 | (2006.01) |
| C07C 25/22 | (2006.01) |
| C09B 3/14 | (2006.01) |
| C09B 3/18 | (2006.01) |
| C09B 3/20 | (2006.01) |
| C07C 67/08 | (2006.01) |
| C07C 41/16 | (2006.01) |
| C07C 41/22 | (2006.01) |
| C07C 41/01 | (2006.01) |
| C07C 253/30 | (2006.01) |
| C09B 1/00 | (2006.01) |
| C09B 5/02 | (2006.01) |
| H01L 51/00 | (2006.01) |
| H01L 51/05 | (2006.01) |
| H01L 51/42 | (2006.01) |
| H01L 51/50 | (2006.01) |

(52) U.S. Cl.
CPC .............. *C07D 495/06* (2013.01); *C07C 25/22* (2013.01); *C07C 41/01* (2013.01); *C07C 41/16* (2013.01); *C07C 41/22* (2013.01); *C07C 43/29* (2013.01); *C07C 67/08* (2013.01); *C07C 69/76* (2013.01); *C07C 253/30* (2013.01); *C07C 255/52* (2013.01); *C07F 7/0818* (2013.01); *C09B 1/00* (2013.01); *C09B 3/14* (2013.01); *C09B 3/18* (2013.01); *C09B 3/20* (2013.01); *C09B 5/026* (2013.01); *H01L 51/0055* (2013.01); *H01L 51/0074* (2013.01); *H01L 51/0094* (2013.01); *C07C 2103/52* (2013.01); *H01L 51/05* (2013.01); *H01L 51/42* (2013.01); *H01L 51/50* (2013.01)

(58) Field of Classification Search
CPC ..................................................... C07D 495/06
USPC ............................................................ 549/31
See application file for complete search history.

(56) References Cited

U.S. PATENT DOCUMENTS

| 4,505,858 A | 3/1985 | Mayer |
| 4,618,694 A | 10/1986 | Iden et al. |
| 6,329,084 B1 | 12/2001 | Tamano et al. |

FOREIGN PATENT DOCUMENTS

| DE | 66611 | 1/1893 |
| DE | 340091 | 9/1921 |
| DE | 498039 | 5/1930 |
| DE | 1 154 799 | 9/1963 |
| DE | 1 958 595 | 11/1970 |
| JP | 2002-12861 A | 1/2002 |

OTHER PUBLICATIONS

King, Med. Chem., Principle and Practice (1994), pp. 206-208.*
International Search Report issued Feb. 27, 2014 in PCT/IB2013/058009.
Luis F. Veiros, et al., "Ability of Substituted Perylenes to Form Organic Conductors", Molecular Crystals and Liquid Crystals, vol. 333, (1999), pp. 259-268.
U.S. Appl. No. 14/758,349, filed Jun. 29, 2015, Wonneberger, et al.
Office Action issued Sep. 9, 2015 in corresponding Chinese Patent Application No. 201380044965.4, 10 pages.
Sun et al., "Gas Phase Reactions of Carbon Cluster Ions with Crotononitrile," The Journal of Physical Chemistry, vol. 98, No. 17, 1994, pp. 4536-4542.

* cited by examiner

*Primary Examiner* — Taofiq A Solola
(74) *Attorney, Agent, or Firm* — Oblon, McClelland, Maier & Neustadt, L.L.P.

(57) ABSTRACT

The present invention provides the compounds of formulae (3) and (1), wherein n is 0 or 1, $R^{11}$ and $R^{12}$ are the same and are selected from the group consisting of CN, $OR^{300}$, $Si(R^{301})_3$, $NHR^{302}$, $NR^{303}R^{304}$, $SR^{305}$ and $R^{306}$, or $R^{11}$ and $R^{12}$ together are selected from the group consisting of (a), (b), and (c) and X is Cl, Br or I, and a process for the preparation of compounds of formula (3) comprising the compounds of formula (1) as key intermediates.
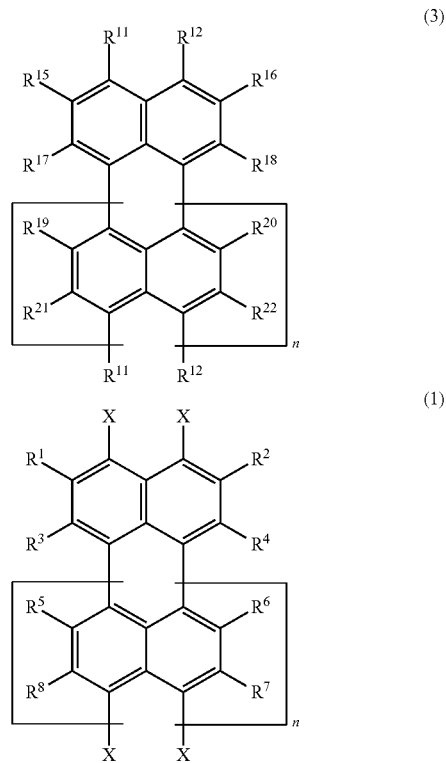
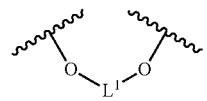
(a)
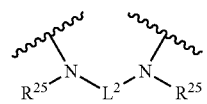
(b)
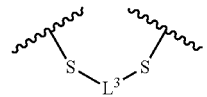
(c)
12 Claims, No Drawings

CONVENIENTLY PREPARED NAPHTHALENE AND PERYLENE DERIVATIVES AS BUILDING BLOCKS FOR ORGANIC ELECTRONIC MATERIALS AND DYESTUFF

The invention relates to naphthalene and perylene derivatives.

Many naphthalene and perylene derivates are important colorants. Beside this traditional application, naphthalene and, in particular, perylene derivatives gain more and more interest in other applications such as in organic field-effect transistors, organic light emitting devices, photovoltaic devices such as dye-sensitized solar cells (DSCs), and xerography.

The design and preparation of naphthalene and perylene derivatives, which are tuned to be suitable for a particular application, are an active area of research.

Naphthalene and perylene derivatives, which are substituted in all four peri-positions, in particular with substituents such as cyano, alkyoxy, aryloxy, silyl, substituted amino, alkylthio, arylthio, alkyl and aryl, could be suitable for many applications.

DE 340091 describes the preparation of 3,4,9,10-tetracyanoperylene from 3,4,9-tricyano-10-bromoperylene. 3,4,9-tricyano-10-bromoperylene was prepared from 3,4,9,10-tetrabromo-perylene, which was obtained by bromination of perylene in nitrobenzene.

JP 2002-012861 describes perylene derivatives, which carry a substituted or unsubstituted amino group in the 1 or 2 position. In particular, JP 2002-012861 describes the preparation of 3,4,9,10-tetraphenylperylene and 3,4,9,10-tetracyanoperylene, both substituted in 1 and 7 position with a substituted amino group, from 1,7-dibromo-3,4,9,10-tetraphenylperylene, respectively, 1,7-dibromoperylene 3,4,9,10-tetracarbonitrile.

Zinke, A.; Pongratz, A., Funke, K. *Chem. Ber.* 1925, 58, 330 to 332 and DE 498 039 describes a process for the halogenation of perylene, wherein the halogenation is effected in the presence of a solvent such as nitrobenzene, and the halogen is employed in statu nascendi. According to the examples 3,9-dichloroperylene, tetrachloroperylene (mp. 350° C.), and hexachloroperylene (mp. 356° C.) are prepared by running an acetic acid solution of hydrogen peroxide into a solution of perylene in nitrobenzene at the same time as an acetic acid solution of concentrated hydrochloric acid is being added. It is said that the tetrachloroperylene is likely to be the 3,4,9,10-tetrachloroperylene. A further substitution of X is not described.

Many naphthalene derivatives, which are chlorinated or brominated in all four pen-positions, are known (DE 66611, Whitehurst, J. S. *J. Chem. Soc.* 1951, 221 to 226, Bassilios, H. F.; Salem, A. Y.; Shawky, M. *Rec. Trav. Chim Pays-Bas* 1962, 81, 209 to 214, DE 1958 595, Mesh, L. A.; Grudtsyn, Y. V. *J. Org. Chem. USSR* 1977, 13, 2384 to 2389, Brady, J. H.; Redhouse, A. D.; Wakefield, B. J. *J. Chem. Res. Miniprint* 1982, 6, 1541 to 1554, Otsubo, T.; Sukenobe, N.; Aso, Y.; Ogura, F. *Chem. Lett.* 1987, 315 to 316, Garcia, R.; Riera, J.; Carilla, J.; Julia, L.; Molins, E., Miravitlles C. *J. Org. Chem.* 1992, 57, 5712, Kodama, T.; Kodani, M.; Takimiya, K.; Aso, Y.; Otsubo, T. *Heteroatom. Chem.* 2001, 12, 287 to 292).

DE 1 154 799 describes the following process

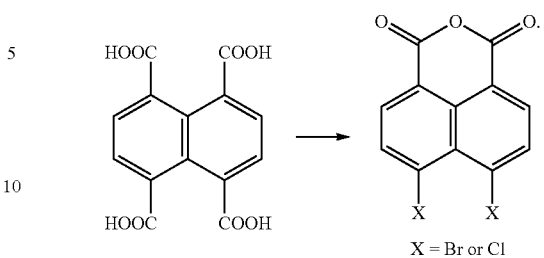

DE 1 154 799 emphasizes that it was not possible to obtain the tetrahalogenated naphthaline. A further substitution of X is not described.

It was the object of the present invention to provide naphthalene and perylene derivatives, which are substituted in all four peri-positions.

The object is solved by the process of claim 1, the compounds of claim 8 and the compounds of claim 12.

The process of the present invention for the preparation of compounds of formula

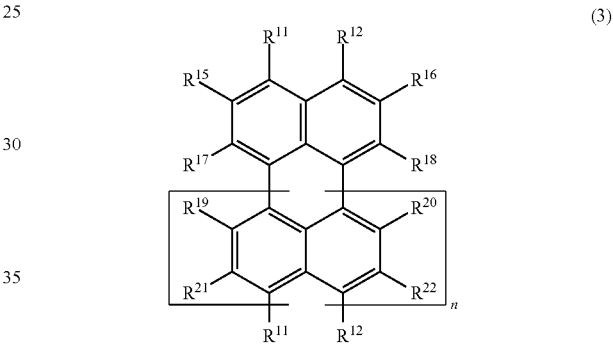

(3)

wherein
n is 0 or 1,
$R^{11}$ and $R^{12}$ are the same and are selected from the group consisting of CN, $OR^{300}$, $Si(R^{301})_3$, $NHR^{302}$, $NR^{303}R^{304}$, $SR^{305}$ and $R^{306}$
wherein
$R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl or $C_{6-14}$-aryl,
wherein
$C_{1-20}$-alkyl, $C_{2-20}$-alkenyl and $C_{2-20}$-alkynyl may be substituted with one or more substituents selected from the group consisting of phenyl, $NR^{3000}R^{3001}$, $O-R^{3002}$ and $S-R^{3003}$ and
$C_{6-14}$-aryl may be substituted with one or more substituents selected from the group consisting of $C_{1-10}$-alkyl, $NR^{3004}R^{3005}$, $O-R^{3006}$ and $S-R^{3007}$,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{11}$ and $R^{12}$ together are selected from the group consisting of

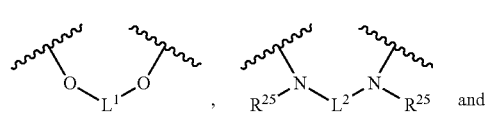

and

-continued

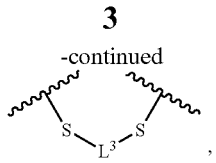

wherein $L^1$ and $L^2$ are $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl, $C_{2-20}$-alkenyl, $C_{2-20}$-alkynyl, $C_{5-8}$-cycloalkyl, or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, O—$R^{3012}$ and S—$R^{3013}$, and $C_{6-14}$-aryl may be substituted with one or more substituents selected from the group consisting of $C_{1-10}$-alkyl, $NR^{3014}R^{3015}$, O—$R^{3016}$ and S—$R^{3017}$, wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl, $L^3$ is a direct bond, $C_{1-6}$-alkylene, $C_{6-14}$-arylene, or $C_{1-6}$-alkylene-$C_{6-14}$-arylene-$C_{1-6}$-alkylene, and $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, O—$R^{3022}$, S—$R^{3023}$, $NO_2$, CN and halogen, $C_{6-14}$-aryl may be substituted with one or more substituents selected from the group consisting of $C_{1-10}$-alkyl, $NR^{3024}R^{3025}$, O—$R^{3026}$, S—$R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

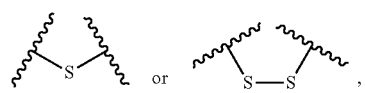

comprises the step of treating a compound of formula (2)

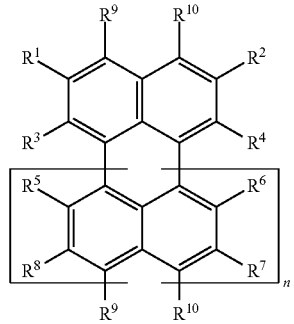

wherein n has the meaning as depicted for formula (3), $R^9$ and $R^{10}$ are the same or different and are COOH or $COOR^{200}$, wherein $R^{200}$ is $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2000}R^{2001}$, O—$R^{2002}$ and S—$R^{2003}$, $C_{6-14}$-aryl may be substituted with one or more substituents selected from the group consisting of $C_{1-10}$-alkyl, $NR^{2004}R^{2005}$, O—$R^{2006}$ and S—$R^{2007}$, wherein $R^{2000}$, $R^{2001}$, $R^{2002}$ and $R^{2003}$, $R^{2004}$, $R^{2005}$, $R^{2006}$ and $R^{2007}$ are the same or different and are $C_{1-10}$-alkyl or phenyl or $R^9$ and $R^{10}$ together are

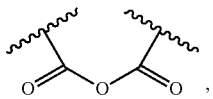 [SMILES: *C(=O)OC(*)=O]

and $R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$ and $C(O)OR^{204}$, wherein $R^{200}$, $R^{201}$, $R^{202}$, $R^{203}$ and $R^{204}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, O—$R^{2012}$, S—$R^{2013}$, $NO_2$, CN and halogen, $C_{6-14}$-aryl may be substituted with one or more substituents selected from the group consisting of $C_{1-10}$-alkyl, $NR^{2014}R^{2015}$, O—$R^{2016}$, S—$R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

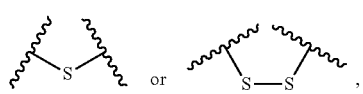

a) with MOH, wherein M is an alkali metal, N($R^{400}R^{401}R^{402}R^{403}$), P($R^{400}R^{401}R^{402}R^{403}$) or hexa($C_{1-10}$-alkyl)guanidinium,
wherein $R^{400}$, $R^{401}$, $R^{402}$ and $R^{403}$ are the same or different and are selected from the group consisting of H, $C_{1-20}$-alkyl, $C_{2-20}$-alkenyl, $C_{2-20}$-alkynyl, $C_{5-8}$-cycloalkyl and $C_{6-14}$-aryl,
wherein
$C_{1-20}$-alkyl, $C_{2-20}$-alkenyl, $C_{2-20}$-alkynyl and $C_{5-8}$-cycloalkyl may be substituted with phenyl,
$C_{6-14}$-aryl may be substituted with $C_{1-10}$-alkyl,
and
b) an X-donor, wherein X is Cl, Br or I,
in order to obtain a compound of formula

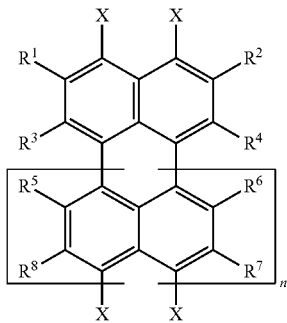

(1)

wherein
X has the meaning as depicted for the X-donor,
n has the meaning as depicted for formula (3),
and
$R^1$, $R^2$, $R^3$, $R^4$, $R^5$, $R^6$, $R^7$ and $R^8$ have the meaning as depicted for formula (2).

$C_{1-10}$-alkyl and $C_{1-20}$-alkyl can be branched or unbranched. Examples of $C_{1-10}$-alkyl are methyl, ethyl, butyl, iso-butyl, sec-butyl, tert-butyl, pentyl, isopentyl, hexyl, heptyl, octyl, 1,1-dimethyl-3,3-dimethylbutyl, nonyl and decyl. Examples of $C_{1-20}$-alkyl are $C_{1-10}$-alkyl, undecyl, dodecyl, tridecyl, tetradecyl, pentadecyl, hexadecyl, heptadecyl, octadecyl, nonadecyl and eicosyl, $C_{2-20}$-alkenyl can be branched or unbranched. Examples of $C_{2-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl, linoleyl ($C_{18}$), linolenyl ($C_{18}$), oleyl ($C_{18}$) and arachidonyl ($C_{20}$).

$C_{2-20}$-alkynyl can be branched or unbranched. Examples of $C_{2-20}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-8}$-cycloalkyl are cyclopentyl, cyclohexyl, cycloheptyl and cyclooctyl.

Examples of $C_{6-14}$-aryl are phenyl and naphthyl.

Examples of halogen are F, Cl, Br and I.

Examples of alkali metals are Na, K and Li.

Examples of N($R^{400}R^{401}R^{402}R^{403}$) are tetra (n-butyl)ammonium and decyl-methyl-dioctyl-ammonium.

Examples of hexa($C_{1-10}$-alkyl)-guanidinium are hexamethylguanidinium and hexaethylguanidinium.

Examples of X-donors are X—X, X-succinimide and N,N"-di-X-isocyanuric acid.

Preferably, $R^{11}$ and $R^{12}$ are the same and are selected from the group consisting of CN, $OR^{300}$ and $Si(R^{301})_3$,
wherein
$R^{300}$ and $R^{301}$ are $C_{1-20}$-alkyl, $C_{2-20}$-alkenyl, $C_{2-20}$-alkynyl or $C_{6-14}$-aryl,
wherein
$C_{1-20}$-alkyl, $C_{2-20}$-alkenyl and $C_{2-20}$-alkynyl may be substituted with one or more substituents selected from the group consisting of phenyl, $NR^{3000}R^{3001}$, O—$R^{3002}$ and S—$R^{3003}$ and
$C_{6-14}$-aryl may be substituted with one or more substituents selected from the group consisting of $C_{1-10}$-alkyl, $NR^{3004}R^{3005}$, O—$R^{3006}$ and S—$R^{3007}$,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{11}$ and $R^{12}$ together are

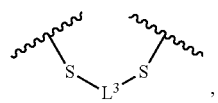

, wherein
$L^3$ is a direct bond, $C_{1-6}$-alkylene, $C_{6-14}$-arylene, or $C_{1-6}$-alkylene-$C_{6-14}$-arylene-$C_{1-6}$-alkylene.

More preferably, $R^{11}$ and $R^{12}$ are the same and are selected from the group consisting of CN, $OR^{300}$ and $Si(R^{301})_3$,
wherein
$R^{300}$ and $R^{301}$ are $C_{1-20}$-alkyl or $C_{6-14}$-aryl,
wherein
$C_{1-20}$-alkyl may be substituted with one or more substituents selected from the group consisting of phenyl, $NR^{3000}R^{3001}$, O—$R^{3002}$ and S—$R^{3003}$ and
$C_{6-14}$-aryl may be substituted with one or more substituents selected from the group consisting of $C_{1-10}$-alkyl, $NR^{3004}R^{3005}$, O—$R^{3006}$ and S—$R^{3007}$,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{11}$ and $R^{12}$ together are

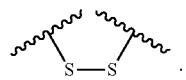

.

Most preferably, $R^{11}$ and $R^{12}$ are the same and are selected from the group consisting of CN, $OR^{300}$ and $Si(R^{301})_3$,
wherein
$R^{300}$ and $R^{301}$ are $C_{1-20}$-alkyl or $C_{6-14}$-aryl,
wherein
$C_{6-14}$-aryl may be substituted with one or more substituents selected from the group consisting of $C_{1-10}$-alkyl, $NR^{3004}R^{3005}$, O—$R^{3006}$ and S—$R^{3007}$,
wherein $R^{3004}$, $R^{3005}$, $R^{3006}$ and $R^{3007}$ are the same or different and are $C_{1-10}$-alkyl or phenyl,
or
$R^{11}$ and $R^{12}$ together are

.

Preferably, n is 1,

Preferably, $R^{15}, R^{16}, R^{17}, R^{18}, R^{19}, R^{20}, R^{21}$ and $R^{22}$ are the same or different and are selected from the group consisting of H, Cl, Br, I, CN and $OR^{311}$, wherein $R^{311}$ is $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O\text{—}R^{3022}$, $S\text{—}R^{3023}$, $NO_2$, CN and halogen, $C_{6-14}$-aryl may be substituted with one or more substituents selected from the group consisting of $C_{1-10}$-alkyl, $NR^{3024}R^{3025}$, $O\text{—}R^{3026}$, $S\text{—}R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

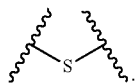

Preferably, if n is 0, $R^{15}$, $R^{16}$, $R^{17}$ and $R^{18}$ are H.

Preferably, if n is 1, $R^{15}$, $R^{16}$, $R^{21}$ and $R^{22}$ are H, and $R^{17}$, $R^{18}$, $R^{19}$ and $R^{20}$, are the same or different and are selected from the group consisting of F, Cl, Br, I, CN, $R^{310}$, $OR^{311}$, $SR^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O\text{—}R^{3022}$, $S\text{—}R^{3023}$, $NO_2$, CN and halogen, $C_{6-14}$-aryl may be substituted with one or more substituents selected from the group consisting of $C_{1-10}$-alkyl, $NR^{3024}R^{3025}$, $O\text{—}R^{3026}$, $S\text{—}R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

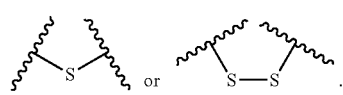

More preferably, if n is 1, $R^{15}$, $R^{16}$, $R^{21}$ and $R^{22}$ are H, and $R^{17}$, $R^{18}$, $R^{19}$ and $R^{20}$ are the same or different and are selected from the group consisting of Cl, Br, I, CN and $OR^{311}$, wherein $R^{311}$ is $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O\text{—}R^{3022}$, $S\text{—}R^{3023}$, $NO_2$, CN and halogen, $C_{6-14}$-aryl may be substituted with one or more substituents selected from the group consisting of $C_{1-10}$-alkyl, $NR^{3024}R^{3025}$, $O\text{—}R^{3026}$, $S\text{—}R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

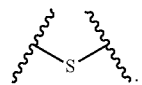

Most preferably, if n is 1, $R^{15}$, $R^{16}$, $R^{21}$ and $R^{22}$ are H, and $R^{17}$, $R^{18}$, $R^{19}$ and $R^{20}$ are the same or different and are selected from the group consisting of Cl, Br, I and CN.

Even most preferably, if n is 1, $R^{15}$, $R^{16}$, $R^{21}$ and $R^{22}$ are H, and $R^{17}$, $R^{18}$, $R^{19}$ and $R^{20}$ are Cl.

Preferably, $R^9$ and $R^{10}$ are the same and are COOH, or $R^9$ and $R^{10}$ together are

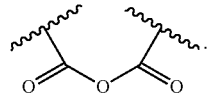 [SMILES: *C(=O)OC(*)=O]

More preferably, $R^9$ and $R^{10}$ together are

Preferably, $R^1$, $R^2$, $R^3$, $R^4$, $R^5$, $R^6$, $R^7$ and $R^8$ are the same or different and are selected from the group consisting of H, Cl, Br, I, CN and $OR^{201}$, wherein $R^{201}$ is $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O\text{—}R^{2012}$, $S\text{—}R^{2013}$, $NO_2$, CN and halogen, $C_{6-14}$-aryl may be substituted with one or more substituents selected from the group consisting of $C_{1-10}$-alkyl, $NR^{2014}R^{2015}$, $O\text{—}R^{2016}$, $S\text{—}R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

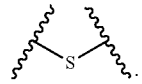

Preferably, if n is 0, $R^1$, $R^2$, $R^3$ and $R^4$ are H.

Preferably, if n=1, $R^1$, $R^2$, $R^7$ and $R^8$ are H, and $R^3$, $R^4$, $R^5$ and $R^6$, are the same or different and are selected from the group consisting of F, Cl, Br, I, CN, $R^{200}$, $OR^{201}$, $SR^{202}$, $OC(O)R^{203}$, and $C(O)OR^{264}$, wherein $R^{200}$, $R^{201}$, $R^{202}$, $R^{203}$ and $R^{204}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O-R^{2012}$, $S-R^{2013}$, $NO_2$, CN and halogen, $C_{6-14}$-aryl may be substituted with one or more substituents selected from the group consisting of $C_{1-10}$-alkyl, $NR^{2014}R^{2015}$, $O-R^{2016}$, $S-R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

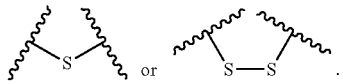

More preferably, if n is 1, $R^1$, $R^2$, $R^7$ and $R^8$ are H, and $R^3$, $R^4$, $R^5$ and $R^6$ are the same or different and are selected from the group consisting of Cl, Br, I, CN and $OR^{201}$, wherein $R^{201}$ is $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O-R^{2012}$, $S-R^{2013}$, $NO_2$, CN and halogen, $C_{6-14}$-aryl may be substituted with one or more substituents selected from the group consisting of $C_{1-10}$-alkyl, $NR^{2014}R^{2015}$, $O-R^{2016}$, $S-R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

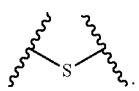

Most preferably, if n is 1, $R^1$, $R^2$, $R^7$ and $R^8$ are H, and $R^3$, $R^4$, $R^5$ and $R^6$ are the same or different and are selected from the group consisting of Cl, Br and $OR^{261}$, wherein $R^{201}$ is $C_{6-14}$-aryl, wherein $C_{6-14}$-aryl may be substituted with $C_{1-10}$-alkyl, or $R^3$ and $R^5$, respectively, $R^4$ and $R^6$ together are

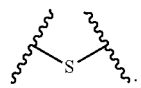

Preferably, M is an alkali metal, more preferably Na.

Preferably, X is Cl or Br, more preferably Br.

Preferably, the compound of formula (2) is first treated with MOH, followed by treatment with the X-donor. Usually the process is performed without the isolation of any intermediate products in a so-called "one pot reaction".

The compound of formula (2) is commercially available or can be obtained by methods known in the art.

Preferably, the X-donor is X—X. More preferably, the X-donor is X—X, wherein X is Cl or Br. Most preferably, the X-donor is X—X, wherein X is Br.

Preferably, the treatment with MOH and the treatment with the X-donor are performed in an aqueous solvent such as water or mixtures of water with a suitable organic solvent such as tetrahydrofuran or dioxane. More preferably, the treatment with MOH and the treatment with the X-donor are performed in water as solvent.

Preferably, the treatment with MOH is performed at a temperature from 10 to 100° C., more preferably from 20 to 60° C.

Preferably, the molar ratio of MOH/compound of general formula (2) is 4/1 to 20/1, more preferably 4/1 to 10/1, most preferably 4/1 to 7/1.

Preferably, the molar ratio of the X-donor/compound of general formula (2) is 4/1 to 30/1, more preferably 4/1 to 20/1, most preferably 4/1 to 17/1.

Preferably, the treatment with the X-donor is performed at a temperature from 10 to 260° C., more preferably from 20 to 120° C., most preferably from 20 to 100° C.

The compound of formula (1) can be isolated by methods known in the art, for example by extraction with a suitable organic solvent such as dichloromethane. After isolation the compound of formula (1) may be further purified by methods known in the art, such as recrystallization or chromatography.

The compounds of formula (3) can be directly obtained from the compounds of formula (1) or via intermediate compounds in a multiple steps by methods known in the art.

For example, the compounds of formula (3), wherein $R^{11}$ and $R^{12}$ are both CN or $OR^{300}$, can be prepared by treating the compound of formula (1) with $M^2CN$ or $M^2OR^{300}$, wherein $M^2$ can be an alkali metal or a transition metal.

For example, the compounds of formula (3), wherein $R^{11}$ and $R^{12}$ both are $Si(R^{301})_3$, can be prepared by treating the compound of formula (1) with an organyl-$M^3$, wherein $M^3$ can be an alkali metal, followed by, $X^2$—$Si(R^{301})_3$, wherein $X^2$ can be halogen.

For example, the compounds of formula (3), wherein $R^{11}$ and $R^{12}$ together are

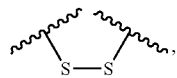

can be prepared by treating the compound of formula (1) with sulphur.

For example, the compounds of formula (3), wherein $R^{11}$ and $R^{12}$ both are $NHR^{302}$, $NR^{303}R^{304}$, respectively, $SR^{305}$ can be prepared by treating the compound of formula (1) with $NH_2R^{302}$, $NHR^{303}R^{304}$, respectively, $HSR^{305}$.

For example, the compounds of formula (3), wherein $R^{11}$ and $R^{12}$ both are $R^{306}$ can be prepared by treating the compound of formula (1) with $R^{306}$ boronic acid in the presence of a suitable catalyst such as $Pd[P(Ph)_3]_4$.

For example, the compounds of formula (3a)

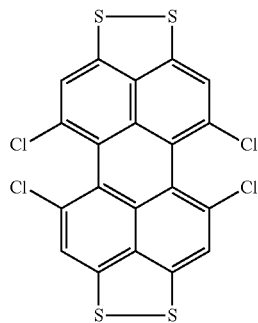

can be prepared by treating the compound of formula (1b)

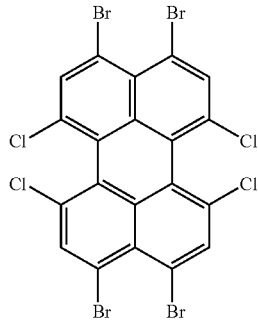

with sulfur.

For example the compound of formula (3b)

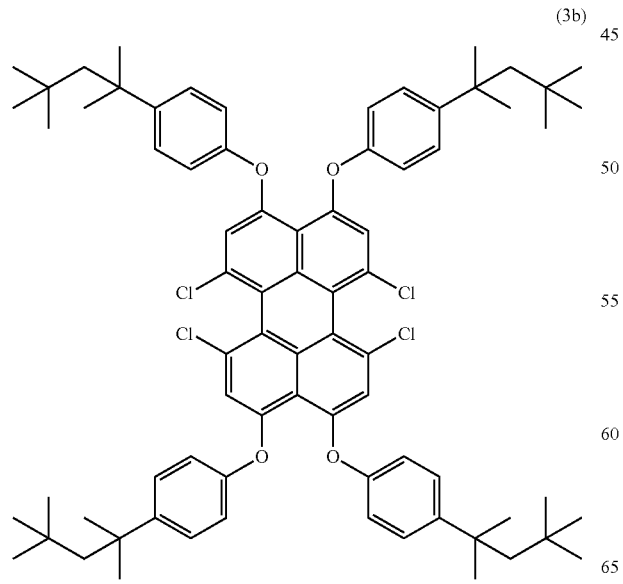

can be prepared by treating the compound of formula (1b)

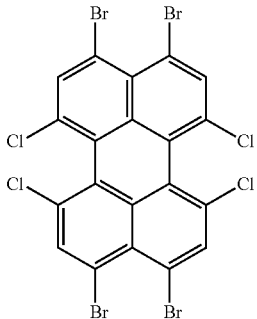

with 4-(2,4,4-trimethylpentan-2-yl)phenol and $K_2CO_3$.

For example, the compound of formula (3c)

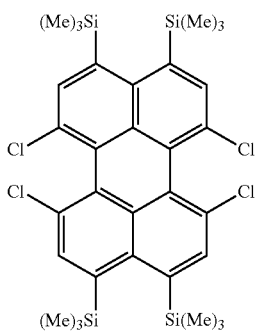

can be prepared by treating the compound of formula (1b)

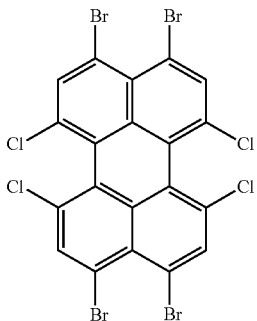

with n-butyl lithium and trimethylsilyl chloride.

For example, the compound of formula (3d)

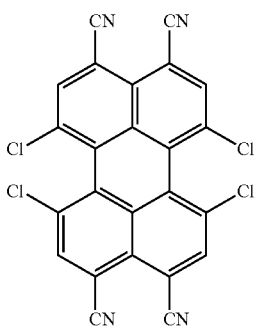

can be prepared by treating a compound of formula

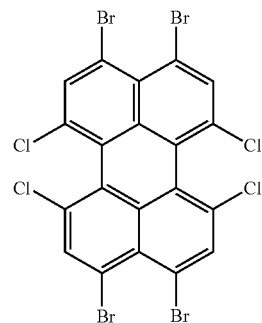

(1b)

with CuCN.

Also part of the present invention are compounds of formula

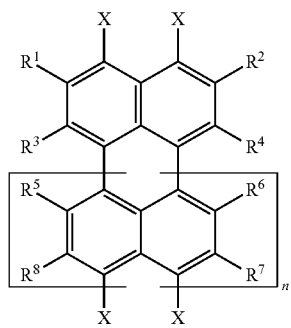

(1)

wherein
X is Cl, Br or I,
n is 0 or 1,
and
$R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$ and $C(O)R^{264}$,
wherein $R^{200}$, $R^{201}$, $R^{202}$, $R^{203}$ and $R^{204}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, O—$R^{2012}$, S—$R^{2013}$, $NO_2$, CN and halogen,
$C_{6-14}$-aryl may be substituted with one or more substituents selected from the group consisting of $C_{1-10}$-alkyl, $NR^{2014}R^{2015}$, O—$R^{2016}$, S—$R^{2017}$, $NO_2$, CN and halogen,
wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl,
or
$R^3$ and $R^5$, respectively, $R^4$ and $R^6$ together are

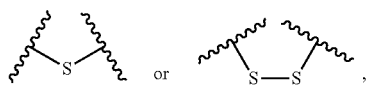

with the proviso
that if n is 0 and X is Cl, $R^1$, $R^2$, $R^3$ and $R^4$ are not H, Cl, CN, $R^{200}$ or $C(O)OR^{204}$, wherein $R^{200}$ and $R^{204}$ are $C_{1-20}$-alkyl,
that if n is 0 and X is Br, $R^1$, $R^2$, $R^3$ and $R^4$ are not H, Br or $R^{200}$, wherein $R^{200}$ is $C_{1-20}$-alkyl, and
that if n is 1 and X is Cl or br, $R^1$, $R^2$, $R^3$, $R^4$, $R^5$, $R^6$, $R^7$ and $R^8$ are not H.

Preferred are compounds of formula

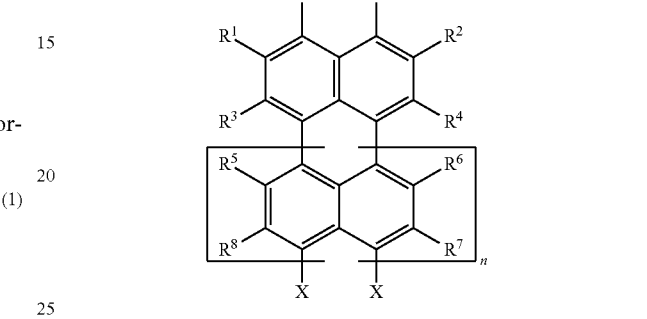

(1)

wherein
X is Cl, Br or I,
n is 1,
and
$R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$ and $C(O)OR^{204}$,
wherein $R^{200}$, $R^{201}$, $R^{202}$, $R^{203}$ and $R^{204}$ are are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, O—$R^{2012}$, S—$R^{2013}$, $NO_2$, CN and halogen,
$C_{6-14}$-aryl may be substituted with one or more substituents selected from the group consisting of $C_{1-10}$-alkyl, $NR^{2014}R^{2015}$, O—$R^{2016}$, S—$R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl
or
$R^3$ and $R^5$, respectively, $R^4$ and $R^6$ together are

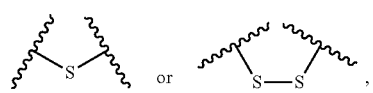

with the proviso
that if n is 1 and X is Cl or Br, $R^1$, $R^2$, $R^3$, $R^4$, $R^5$, $R^6$, $R^7$ and $R^8$ are not H.

More preferred are compounds of formula

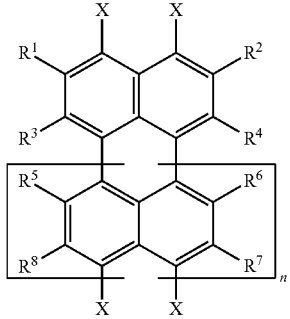

wherein

X is Cl, Br or I, n is 1, and $R^1$, $R^2$, $R^7$ and $R^8$ are H, and $R^3$, $R^4$, $R^5$ and $R^6$, are the same or different and are selected from the group consisting of F, Cl, Br, I, CN, $R^{200}$, $OR^{201}$, $SR^{202}$, $OC(O)R^{203}$ and $C(O)OR^{204}$, wherein $R^{200}$, $R^{201}$, $R^{202}$, $R^{203}$ and $R^{204}$ are are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, O—$R^{2012}$, S—$R^{2013}$, $NO_2$, CN and halogen, $C_{6-14}$-aryl may be substituted with one or more substituents selected from the group consisting of $C_{1-10}$-alkyl, $NR^{2014}R^{2015}$, O—$R^{2016}$, S—$R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

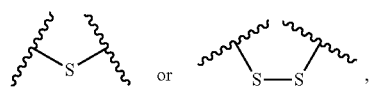

The preferences of n, $R^1$, $R^2$, $R^3$, $R^4$, $R^5$, $R^6$, $R^7$, $R^8$ and X given above for the process for the preparation of compounds of formula (3), also apply to the compounds of formula (1).

In particular preferred are the following compounds

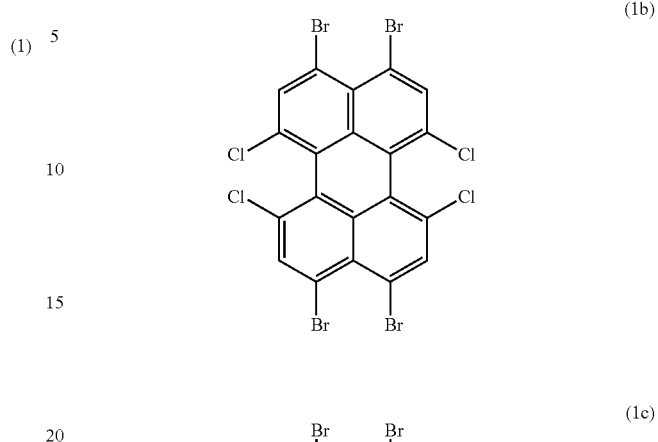

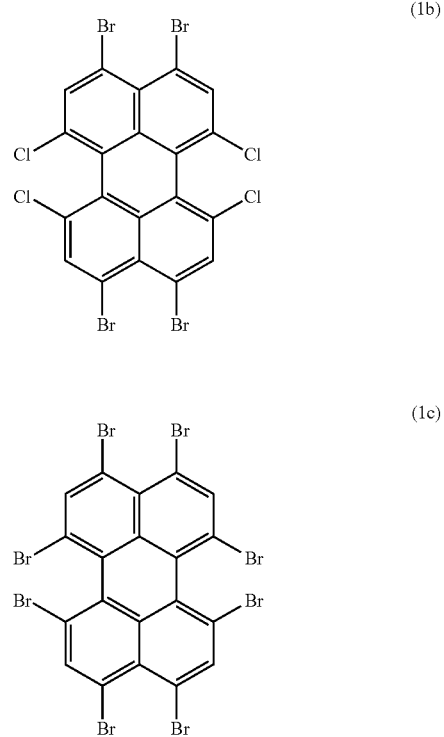

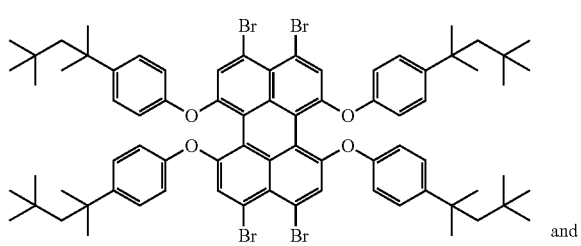

and

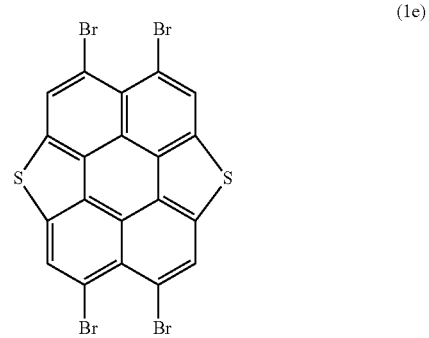

The compounds of formula (1) are versatile building blocks.

Also part of the present invention are compounds of formula

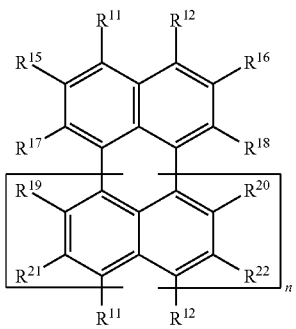
(3)

wherein
n is 0 or 1,
$R^{11}$ and $R^{12}$ are the same and are selected from the group consisting of CN, $OR^{300}$, $Si(R^{301})_3$, $NHR^{302}$, $NR^{303}R^{304}$, $SR^{305}$ and $R^{306}$
wherein
$R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl or $C_{6-14}$-aryl,
wherein
$C_{1-20}$-alkyl, $C_{2-20}$-alkenyl and $C_{2-20}$-alkynyl may be substituted with one or more substituents selected from the group consisting of phenyl, $NR^{3000}R^{3001}$, O—$R^{3002}$ and S—$R^{3003}$ and
$C_{6-14}$-aryl may be substituted with one or more substituents selected from the group consisting of $C_{1-10}$-alkyl, $NR^{3004}R^{3005}$, O—$R^{3006}$ and S—$R^{3007}$,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{11}$ and $R^{12}$ together are selected from the group consisting of

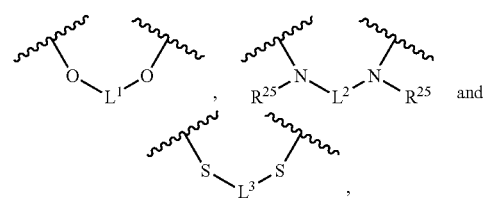

wherein
$L^1$ and $L^2$ are $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, O—$R^{3012}$ and S—$R^{3013}$, and
$C_{6-14}$-aryl may be substituted with one or more substituents selected from the group consisting of $C_{1-10}$-alkyl, $NR^{3014}R^{3015}$, O—$R^{3016}$ and S—$R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
$L^3$ is a direct bond, $C_{1-6}$-alkylene, $C_{6-14}$-arylene, or $C_{1-6}$-alkylene-$C_{6-14}$-arylene-$C_{1-6}$-alkylene,
and $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$,
wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, O—$R^{3022}$, S—$R^{3023}$, $NO_2$, CN and halogen,
$C_{6-14}$-aryl may be substituted with one or more substituents selected from the group consisting of $C_{1-10}$-alkyl, $NR^{3024}R^{3025}$, O—$R^{3026}$, S—$R^{3027}$, $NO_2$, CN and halogen,
wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl,
or
$R^{17}$ and $R^{19}$, respectively, $R^{18}$ and $R^{20}$ together are

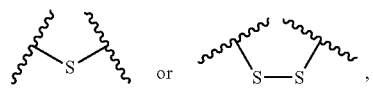

with the proviso that if
n is 0, $R^{11}$ and $R^{12}$ are both CN, then $R^{15}$, $R^{16}$, $R^{17}$ and $R^{18}$ are not all H, and that if
n is 1, $R^{11}$ and $R^{12}$ are both CN or phenyl, and $R^{15}$, $R^{16}$, $R^{18}$, $R^{19}$, $R^{20}$, $R^{21}$ and $R^{22}$ are H, then $R^{17}$ and $R^{20}$ are not Br.
Preferred are the compounds of formula

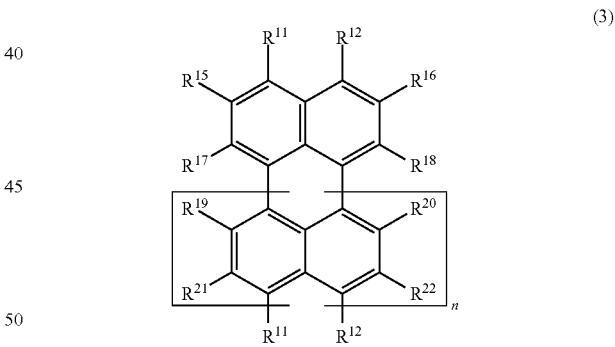
(3)

wherein
n is 0 or 1,
$R^{11}$ and $R^{12}$ are the same and are selected from the group consisting of CN, $OR^{300}$ and $Si(R^{301})_3$,
wherein
$R^{300}$ and $R^{301}$ are $C_{1-20}$-alkyl, $C_{2-20}$-alkenyl, $C_{2-20}$-alkynyl or $C_{6-14}$-aryl,
wherein
$C_{1-20}$-alkyl, $C_{2-20}$-alkenyl and $C_{2-20}$-alkynyl may be substituted with one or more substituents selected from the group consisting of phenyl, $NR^{3000}R^{3001}$, O—$R^{3002}$ and S—$R^{3003}$ and
$C_{6-14}$-aryl may be substituted with one or more substituents selected from the group consisting of $C_{1-10}$-alkyl, $NR^{3004}R^{3005}$, O—$R^{3006}$ and S—$R^{3007}$, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{11}$ and $R^{12}$ together are

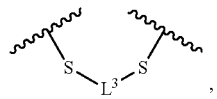, wherein $L^3$ is a direct bond, $C_{1-6}$-alkylene, $C_{6-14}$-arylene, or $C_{1-6}$-alkylene-$C_{6-14}$-arylene-$C_{1-6}$-alkylene, and $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O$—$R^{3022}$, $S$—$R^{3023}$, $NO_2$, CN and halogen, $C_{6-14}$-aryl may be substituted with one or more substituents selected from the group consisting of $C_{1-10}$-alkyl, $NR^{3024}R^{3025}$, $O$—$R^{3026}$, $S$—$R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

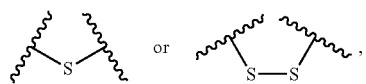

with the proviso that if n is 0, $R^{11}$ and $R^{12}$ are both CN, then $R^{15}$, $R^{16}$, $R^{17}$ and $R^{18}$ are not all H, and that if n is 1, $R^{11}$ and $R^{12}$ are both CN or phenyl, and $R^{15}$, $R^{16}$, $R^{18}$, $R^{19}$, $R^{20}$, $R^{21}$ and $R^{22}$ are H, then $R^{17}$ and $R^{20}$ are not Br.

More preferred are compounds of formula

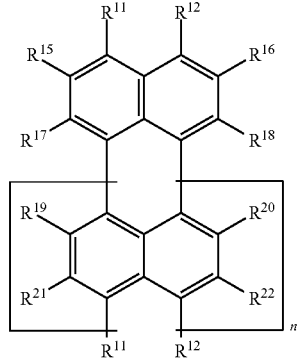

(3)

wherein n is 1, $R^{11}$ and $R^{12}$ are the same and are selected from the group consisting of CN, $OR^{300}$ and $Si(R^{301})_3$, wherein $R^{300}$ and $R^{301}$ are $C_{1-20}$-alkyl, $C_{2-20}$-alkenyl, $C_{2-20}$-alkynyl or $C_{6-14}$-aryl, wherein $C_{1-20}$-alkyl, $C_{2-20}$-alkenyl and $C_{2-20}$-alkynyl may be substituted with one or more substituents selected from the group consisting of phenyl, $NR^{3000}R^{3001}$, $O$—$R^{3002}$ and $S$—$R^{3003}$ and $C_{6-14}$-aryl may be substituted with one or more substituents selected from the group consisting of $C_{1-10}$-alkyl, $NR^{3004}R^{3005}$, $O$—$R^{3006}$ and $S$—$R^{3007}$, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{11}$ and $R^{12}$ together are

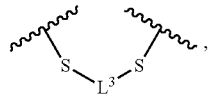, wherein $L^3$ is a direct bond, $C_{1-6}$-alkylene, $C_{6-14}$-arylene, or $C_{1-6}$-alkylene-$C_{6-14}$-arylene-$C_{1-6}$-alkylene, and $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O$—$R^{3022}$, $S$—$R^{3023}$, $NO_2$, CN and halogen, $C_{6-14}$-aryl may be substituted with one or more substituents selected from the group consisting of $C_{1-10}$-alkyl, $NR^{3024}R^{3025}$, $O$—$R^{3026}$, $S$—$R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or R$^{17}$ and R$^{19}$, respectively, R$^{18}$ and R$^{20}$ together are

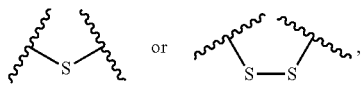

with the proviso
that if n is 1, R$^{11}$ and R$^{12}$ are both CN or phenyl, and R$^{15}$, R$^{16}$, R$^{18}$, R$^{19}$, R$^{20}$, R$^{21}$ and R$^{22}$ are H, then R$^{17}$ and R$^{20}$ are not Br.

Even more preferred are compounds of formula

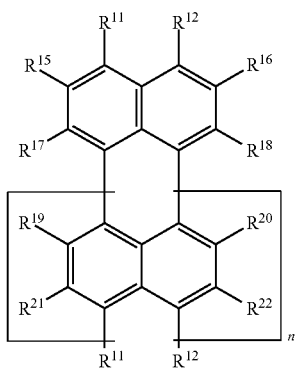

(3)

wherein
n is 1,
R$^{11}$ and R$^{12}$ are the same and are selected from the group consisting of CN, OR$^{300}$ and Si(R$^{301}$)$_3$,
wherein
R$^{300}$ and R$^{301}$ are C$_{1-20}$-alkyl, C$_{2-20}$-alkenyl, C$_{2-20}$-alkynyl or C$_{6-14}$-aryl,
wherein
C$_{1-20}$-alkyl, C$_{2-20}$-alkenyl and C$_{2-20}$-alkynyl may be substituted with one or more substituents selected from the group consisting of phenyl, NR$^{3000}$R$^{3001}$, O—R$^{3002}$ and S—R$^{3003}$ and
C$_{6-14}$-aryl may be substituted with one or more substituents selected from the group consisting of C$_{1-10}$-alkyl, NR$^{3004}$R$^{3005}$, O—R$^{3006}$ and S—R$^{3007}$,
wherein R$^{3000}$, R$^{3001}$, R$^{3002}$, R$^{3003}$, R$^{3004}$, R$^{3005}$, R$^{3006}$ and R$^{3007}$ are the same or different and are C$_{1-10}$-alkyl or phenyl,
or
R$^{11}$ and R$^{12}$ together are

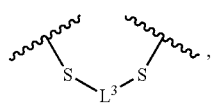

wherein
L$^3$ is a direct bond, C$_{1-6}$-alkylene, C$_{6-14}$-arylene, or C$_{1-6}$-alkylene-C$_{6-14}$-arylene-C$_{1-6}$-alkylene,
and
R$^{15}$, R$^{16}$, R$^{21}$ and R$^{22}$ are H, and R$^{17}$, R$^{18}$, R$^{19}$ and R$^{20}$, are the same or different and are selected from the group consisting of F, Cl, Br, I, CN, R$^{310}$, OR$^{311}$, SR$^{312}$, OC(O)R$^{313}$ and C(O)OR$^{314}$, wherein R$^{310}$, R$^{311}$, R$^{312}$, R$^{313}$ and R$^{314}$ are C$_{1-20}$-alkyl, C$_{2-20}$-alkenyl, C$_{2-20}$-alkynyl, C$_{5-8}$-cycloalkyl or C$_{6-14}$-aryl,
wherein
C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{3020}$R$^{3021}$, O—R$^{3022}$, S—R$^{3023}$, NO$_2$, CN and halogen,
C$_{6-14}$-aryl may be substituted with one or more substituents selected from the group consisting of C$_{1-10}$-alkyl, NR$^{3824}$R$^{3025}$, O—R$^{3026}$, S—R$^{3027}$, NO$_2$, CN and halogen,
wherein R$^{3020}$, R$^{3021}$, R$^{3022}$, R$^{3023}$, R$^{3024}$, R$^{3025}$, R$^{3026}$ and R$^{3027}$ are the same or different and are C$_{1-10}$-alkyl or phenyl,
or
R$^{17}$ and R$^{19}$, respectively, R$^{18}$ and R$^{20}$ together are

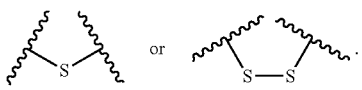

Most preferred are compounds of formula

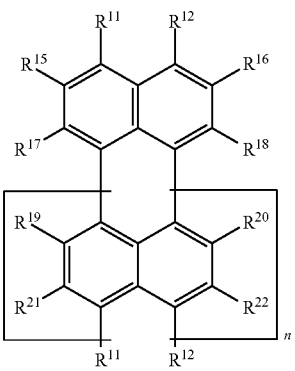

(3)

wherein
n is 1,
R$^{11}$ and R$^{12}$ together are

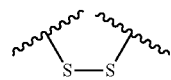

and
R$^{15}$, R$^{16}$, R$^{21}$ and R$^{22}$ are H, and R$^{17}$, R$^{18}$, R$^{19}$ and R$^{20}$, are the same or different and are selected from the group consisting of F, Cl, Br, I, CN, R$^{310}$, OR$^{311}$, SR$^{312}$, OC(O)R$^{313}$ and C(O)OR$^{314}$,
wherein R$^{310}$, R$^{311}$, R$^{312}$, R$^{313}$ and R$^{314}$ are C$_{1-20}$-alkyl, C$_{2-20}$-alkenyl, C$_{2-20}$-alkynyl, C$_{5-8}$-cycloalkyl or C$_{6-14}$-aryl,
wherein
C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{3020}$R$^{3021}$, O—R$^{3022}$, S—R$^{3023}$, NO$_2$, CN and halogen, $C_{6-14}$-aryl may be substituted with one or more substituents selected from the group consisting of $C_{1-10}$-alkyl, $NR^{3924}R^{3025}$, $O-R^{3026}$, $S-R^{3027}$, $NO_2$, CN and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

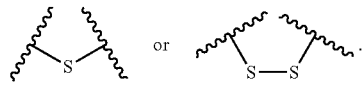

In particular preferred are following compounds

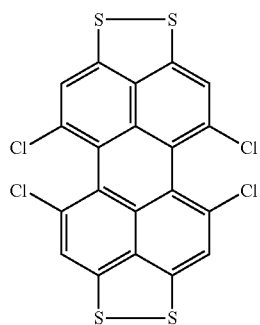

(3a)

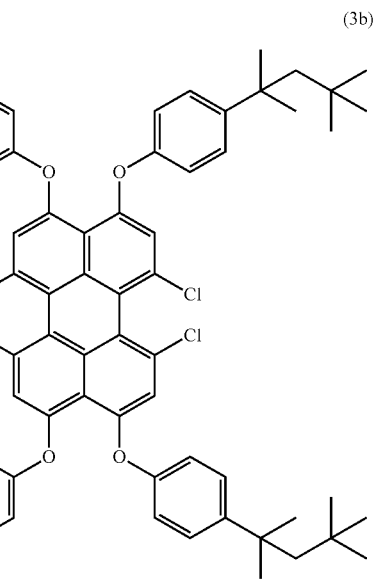

(3b)

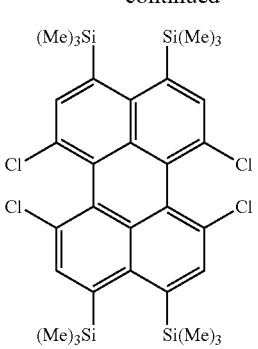

(3c)

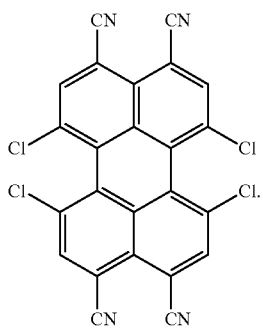

and (3d)

The compounds of formula (3) can be used in various applications, for example as colorants or dyes, or in electronic devices such in organic field-effect transistors, organic light emitting devices and in photovoltaic devices such as dye-sensitized solar cells (DSCs).

Also part of the invention is the use of the compounds of formula (3) in electronic devices.

Also part of the invention is the use of the compounds of formula (3) as dye.

The process of the present invention is advantageous as it allows the convenient preparation of compounds of formula (3).

The key intermediates of the process of the present invention for the preparation of the compounds of formula (3) are the compounds of formula (1) carrying four X-groups, wherein X is Cl, Br or I, in the peri-positions. The compounds of formula (1) are versatile building blocks, which allow the easy introduction of various substituents in the peri-positions by methods known in the art. In case, the compounds of formula (1) also carry suitable substituents such as Cl in the $R^1$, $R^2$, $R^3$, $R^4$, $R^5$, $R^6$, $R^7$ and/or $R^8$ positions, these substituents can also be easily replaced with other substituents.

The compounds of formula (1) can be prepared in a very convenient and economic manner from the compounds of formula (2) The compounds of formula (2), especially the compounds of formula (2), wherein $R^9$ and $R^{10}$ together are

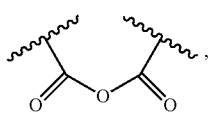 [SMILES: *C(=O)OC(*)=O]

are readily available and of low cost. The compounds of formula (1) are usually obtained in high yields (for example higher than 80%), especially when n is 1, X is Br, and $R^1$, $R^2$, $R^7$ and $R^8$ are H, and $R^3$, $R^4$, $R^5$ and $R^6$ are the same and are selected from the group consisting of H, Cl, and Br, or $R^3$ and $R^5$, respectively, $R^4$ and $R^6$ together are

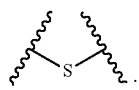 [SMILES: *S*]

Steps a) and b) can be performed at moderate temperatures, for example at temperatures below 100° C. In addition, the steps a) and b) can be performed in an aqueous solvent such as water, and in a so-called "one pot reaction".

EXAMPLES

Example 1

Preparation of Compound 1a

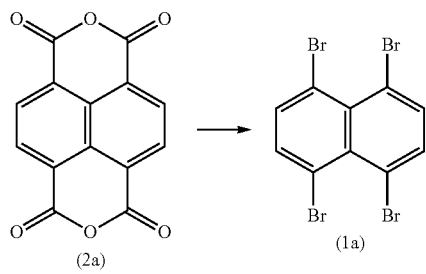 [SMILES: O=C1OC(=O)c2ccc3c4c(ccc1c24)C(=O)OC3=O ; Brc1ccc(Br)c2c(Br)ccc(Br)c12]

20 ml 1M NaOH was added to a suspension of compound 2a (4.00 mmol) in 20 ml water and the mixture was stirred to obtain a limpid solution. Bromine (1.0 ml, 3.11 g) was added in one portion and the reaction mixture was stirred at 90-95° C. for 24 h. The precipitate was filtered and dried. The crude solid was extracted with dichloromethane. Organic solvent was evaporated to dryness and compound 1a was purified by column chromatography using hexane as eluent on silica. Yield 180 mg (10%). FD-Mass: calc.: 443.75. found: 444.0. $^1$H-NMR ($\delta$(ppm), $CD_2Cl_2$): 7.66 (s, 4H, CH); $^{13}$C-NMR ($\delta$(ppm), $CD_2Cl_2$): 120.54 (4C, CBr); 130.49 (2C, C); 135.91 (4C, CH).

Example 2

Preparation of Compound 1b

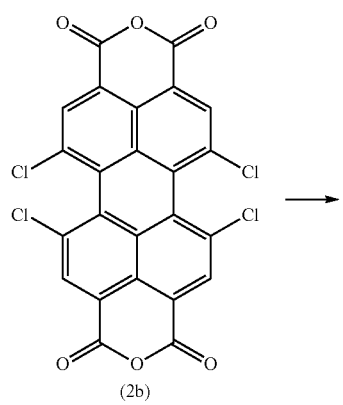

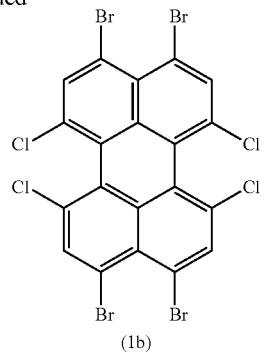

10 ml 1M NaOH was added to a suspension of compound 2b (2.00 mmol) in 20 ml water and the mixture was stirred at 55° C. for 30 min. Bromine (1.0 ml) was added and reaction mixture was stirred for 24 h. The precipitate was filtered and dried. Crude compound 1b was purified by sublimation (1.27 g; 90%) or recrystallization from 1,2-dichlorobenzene (1.17 g; 83%). FD-Mass: calc.: 705.67. found: 706.0. MALDI-TOF: calc.: 705.67. found: 705.75. Elemental analysis: calc.: % C, 34.04; % H, 0.57. found: % C, 34.23; % H, 0.70. $^1$H-NMR ($\delta$(ppm), 1,2-dichlorobenzene-$d_4$): 7.80 (s, 4H).

Example 3

Preparation of Compound 1C

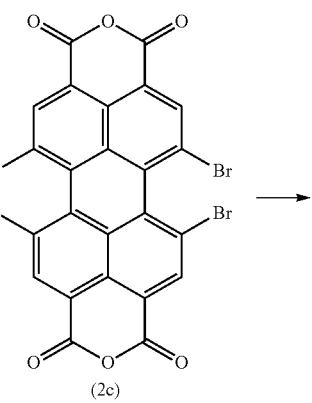

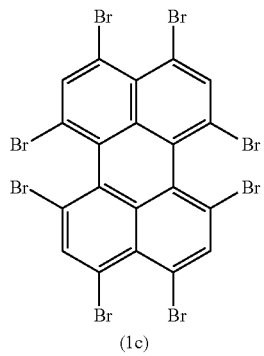

10 ml 1M NaOH was added to a suspension of compound 2c (1.42 g, 2.00 mmol) in 30 ml water and the mixture was stirred at 55° C. for 30 min. Bromine (1.0 ml) was added and reaction mixture was stirred for 24 h. The precipitate was filtered and dried (1.70 g, 96%). The crude compound 1c was purified by recrystallization from 1,2-dichlorobenzene (1.47 g; 83%). FD-Mass: calc.: 883.48. found: 883.7. Elemental analysis: calc.: % C, 27.19; % H, 0.46. found: % C, 27.34; % H, 0.53. $^1$H-NMR (δ(ppm), 1,2-dichlorobenzene-d$_4$): 7.96 (s, 4H).

Example 4

Preparation of Compound 1d

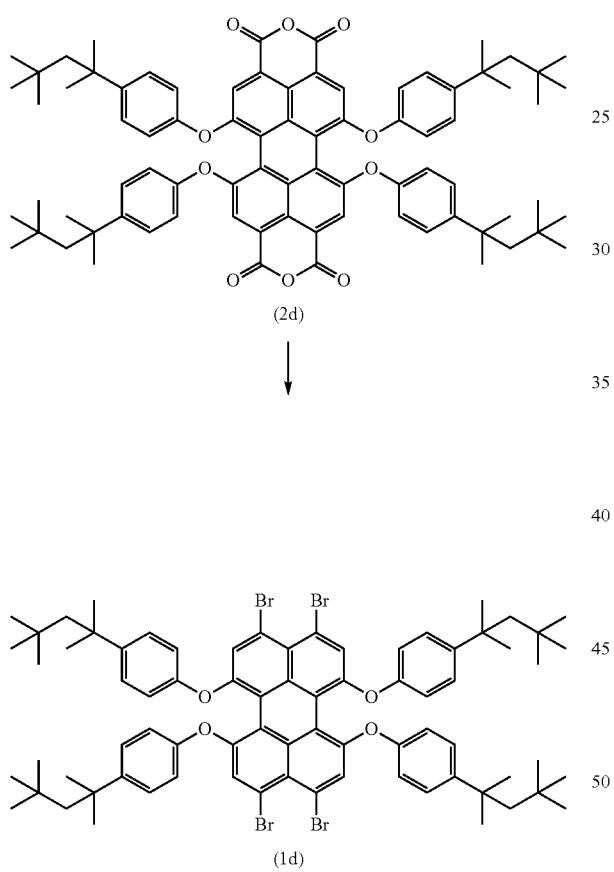

After adding 3 ml 1M NaOH to a solution of compound 2d (0.50 mmol) in 10 ml water THF was added to obtain a clear solution. Bromine (0.40 ml) was added in one portion and the reaction mixture was stirred at room temperature for 0.5 to 1 h (TLC monitoring). A Solution of Na$_2$SO$_3$ (1 g in 10 ml water) was added and stirred for 20 min. Compound 1d was extracted with dichloromethane and purified by column chromatography using hexane as eluent on silica. Yield 5-30 mg (1-6%). $^1$H-NMR (δ(ppm), CD$_2$Cl$_2$): 0.67 (s, 36H, CH$_3$); 1.27 (s, 12H, CH$_3$); 1.28 (s, 12H, CH$_3$); 1.65 (s, 8H, CH$_2$); 6.72 (d, 8H, $^3J_{HH}$=8.7 Hz); 7.19 (d, 8H, $^3J_{HH}$=8.7 Hz); 7.32 (s, 4H). FD-Mass: calc.: 1385.13. found: 1385.9.

Example 5

Preparation of Compound 2e

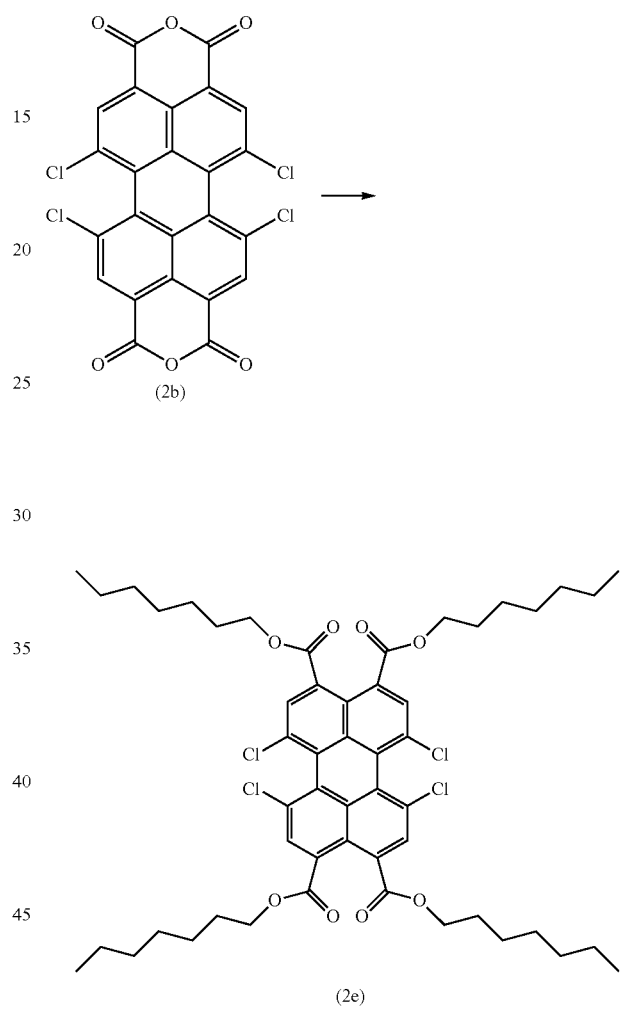

1M NaOH (22 ml) was added to a mixture of compound 2b (2.65 g, 5.00 mmol) and 18 ml water under argon. The mixture was stirred at 70° C. for 30 min and 1 ml Aliquat 336 (Stark' catalyst) was added and stirred additional 10 min at the same temperature. 1-Iodoheptane was added and the reaction mixture was refluxed for 2 h. After cooling down to room temperature, the mixture was extracted with dichloromethane. The solvent was removed under vacuum and crude compound 2e was purified by column chromatography (silica gel, petroleum ether/dichloromethane). Yield 4.315 g (90%) as orange oil. FD-Mass: calc.: 958.87. found: 959.7. $^1$H-NMR (δ(ppm), CDCl$_3$): 0.82 (t, 12H, CH$_3$, $^3J_{HH}$=6.7 Hz); 1.18-1.43 (m, 32H, CH$_2$); 1.74 (p, 8H, $^3J_{HH}$=6.9 Hz, CH$_2$); 4.21-4.34 (m, 8H, CH$_2$O); 8.01 (s, 4H, CH-perylene). $^{13}$C-

NMR (δ(ppm), CDCl₃): 14.20 (4C, CH₃); 22.73 (4C, CH₂); 26.06 (4C, CH₂); 28.66 (4C, CH₂); 29.11 (4C, CH₂); 31.84 (4C, CH₂); 66.48 (4C, CH₂O); 123.24 (2C); 127.32 (4C); 130.90 (4C); 132.12 (4C); 133.67 (4C); 134.06 (2C); 167.11 (4C, CO). Elemental analysis calcd (%) for $C_{52}H_{64}Cl_4O_8$: C, 65.13; H, 6.73. found: C, 65.17; H, 6.87.

Example 6

Preparation of Compound 2f

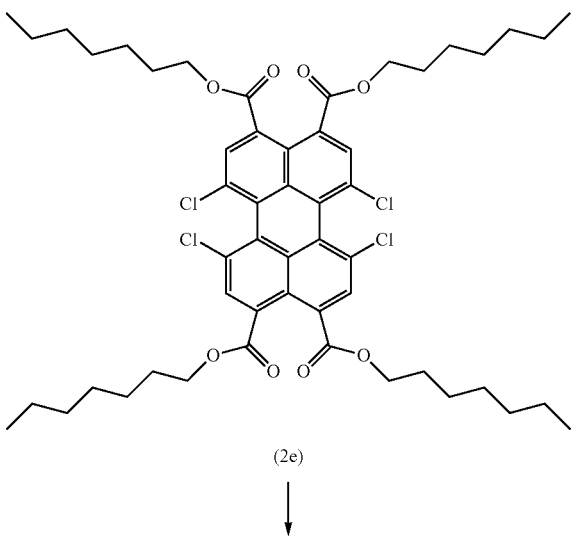

(2e)

↓

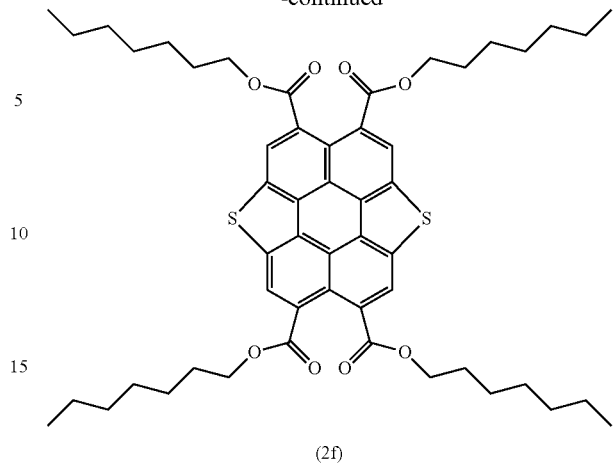

(2f)

Pd(PPh₃)₄ (780 mg, 0.67 mmol) and Bu₃SnSSnBu₃ (3.67 g, 6.00 mmol) were added to a solution of compound 2e (2.60 g, 2.71 mmol) in 100 ml toluene under argon. The mixture was stirred and refluxed for 24 h. The solvent was removed under vacuum and the crude compound 2f was washed with methanol and purified by column chromatography (silica gel, petroleum ether/ethyl acetate). Yield 1.58 g (66%). ¹H-NMR (δ(ppm), CDCl₃): 0.83 (t, 12H, CH₃, $^3J_{HH}$=6.9 Hz); 1.26-1.48 (m, 32H, CH₂); 1.83 (p, 8H, $^3J_{HH}$=6.9 Hz, CH₂); 4.42 (t, 8H, CH₂O, $^3J_{HH}$=6.9 Hz); 8.74 (s, 4H, CH-perylene). ¹³C-NMR (δ(ppm), CDCl₃): 14.22 (4C, CH₃); 22.78 (4C, CH₂); 26.26 (4C, CH₂); 28.91 (4C, CH₂); 29.24 (4C, CH₂); 31.92 (4C, CH₂); 66.22 (4C, CH₂O); 120.98 (2C); 121.54 (2C); 125.31 (4C); 129.60 (4C); 131.13 (4C); 136.83 (4C); 168.61 (4C, CO). Elemental analysis calcd (%) for $C_{52}H_{64}O_8S_2$: C, 70.88; H, 7.32; S, 7.28. found: C, 70.85; H, 76.48; S, 7.22.

Example 7

Preparation of Compound 2g

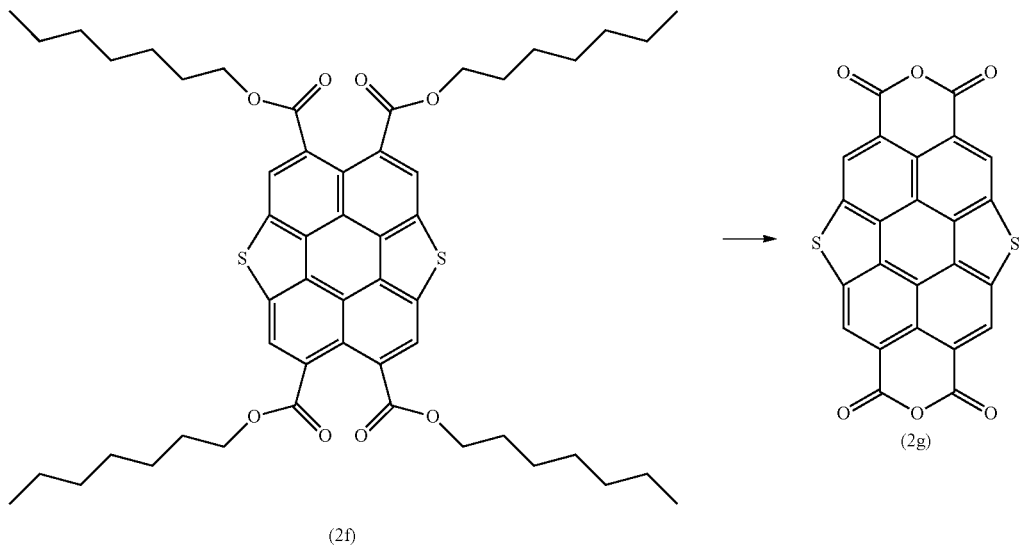 [SMILES: CCCCCCCOC(=O)c1cc2sc3cc(C(=O)OCCCCCCC)c4c(C(=O)OCCCCCCC)cc5sc6cc(C(=O)OCCCCCCC)c1c1c2c3c4c5c61 ; O=c1oc(=O)c2cc3sc4cc5c(=O)oc(=O)c6cc7sc8cc1c2c1c8c7c(c65)c4c31]

(2f) → (2g)

KOH (2.25 g, 34 mmol) and 5 ml water were added to a solution of compound 2f (1.5 g, 1.70 mmol) in 100 ml 2-propanol. The reaction mixture was refluxed overnight. After cooling the reaction mixture was poured onto ice/10% hydrochloric acid. The precipitate was filtered, washed with water and methanol and dried. The solid was suspended in acetic acid (50 ml) and stirred at 70° C. for 5 h. The acetic acid was removed under vacuum. The crude compound 2g was used without further purification. Yield 0.75 g (98%). FD-Mass: calc.: 452.41. found: 453.2.

Example 8

Preparation of Compound 1e

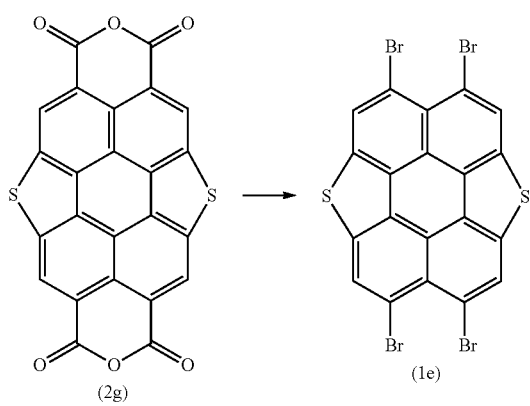 [SMILES: O=c1oc(=O)c2cc3sc4cc5c(=O)oc(=O)c6cc7sc8cc1c2c1c8c7c(c65)c4c31 ; Brc1cc2sc3cc(Br)c4c(Br)cc5sc6cc(Br)c1c1c2c3c4c5c61]

(2g) (1e)

4.5 ml 1M NaOH was added to a suspension of compound 2g (0.455 g, 1.00 mmol) in 20 ml water and the mixture was stirred at 30° C. for 20 min. Bromine (0.21 ml, 4.1 mmol) was added and the reaction mixture was stirred for 10 min at 30° C. The precipitate was filtered, washed with water and dried. The crude compound 1e was suspended in THF (20 ml) and filtered, washed and dried (0.56 g; 89%). MALDI-TOF: calc.: 627.99. found: 627.8 Elemental analysis calcd (%) for $C_{20}H_4Br_4S_2$: C, 38.25; H, 0.64; S, 10.21. found: C, 37.95; H, 1.39; S, 9.65.

Example 9

Preparation of Compound 3a

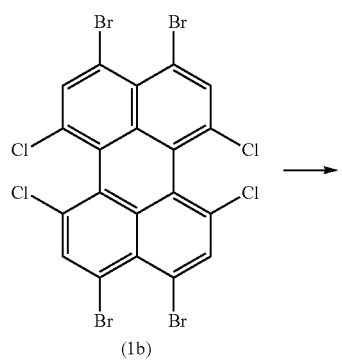

(1b)

-continued

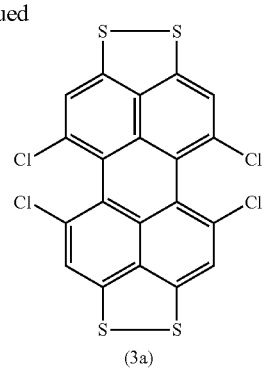

(3a)

A suspension of 3,4,9,10-tetrabromo-1,6,7,12-tetrachloroperylene (0.71 g, 1.00 mmol) and sulfur (0.26 g, 8.0 mmol) in 40 ml NMP was stirred at 190° C. for 3 h. After cooling down to room temperature the reaction mixture was poured into water. The precipitate was filtered, washed with water and dried. The crude compound 3a was purified by column chromatography using dichloromethane as eluent on silica (0.50 g, 97%). FD-Mass: calc.: 514.32. found: 514.1. $^1$H-NMR (δ(ppm), DMSO-$d_6$): 7.72 (s, 4H).

Example 10

Preparation of Compound 3b

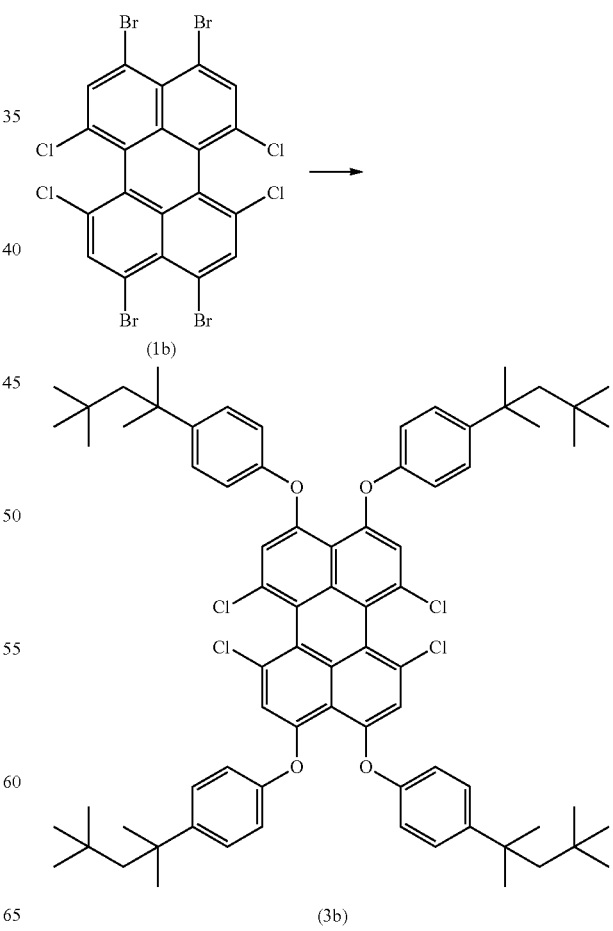

(1b)

(3b)

A mixture of compound 1b (706 mg, 1 mmol), 4-(2,4,4-trimethylpentan-2-yl)phenol (1240 mg, 6 mmol) and $K_2CO_3$ (830 mg, 6 mmol) in 30 ml NMP was stirred at 120° C. for 5 h. The mixture was cooled down to room temperature and dichloromethane (100 ml) was added. The solution was washed several times with water, dried and evaporated. Crude compound 3b was purified by column chromatography using hexane/dichloromethane as eluent on silica. Yield 890 mg (74%). $^1$H-NMR ($\delta$(ppm), $CD_2Cl_2$): 0.66 (s, 36H, $CH_3$); 1.27 (s, 24H, $CH_3$); 1.65 (s, 8H, $CH_2$); 6.72 (d, 8H, $^3J_{HH}$=8.7 Hz); 6.88 (s, 4H); 7.24 (d, 8H, $^3J_{HH}$=8.8 Hz). $^{13}$C-NMR ($\delta$(ppm), $CD_2Cl_2$): 31.98 (4C, $CH_3$); 32.01 (4C, $CH_3$); 32.15 (12C, $CH_3$); 32.83 (4C, $CH_2$); 38.77 (4C); 57.47 (4C); 116.29 (2C); 117.98 (4C); 118.61 (8C, CH); 121.30 (4C); 128.20 (8C, CH); 133.66 (4C); 137.32 (2C); 146.44 (4C, CH); 154.01 (4C); 154.98 (4C). FD-Mass: calc.: 1207.32. found: 1208.1.

Example 11

Preparation of Compound 3c

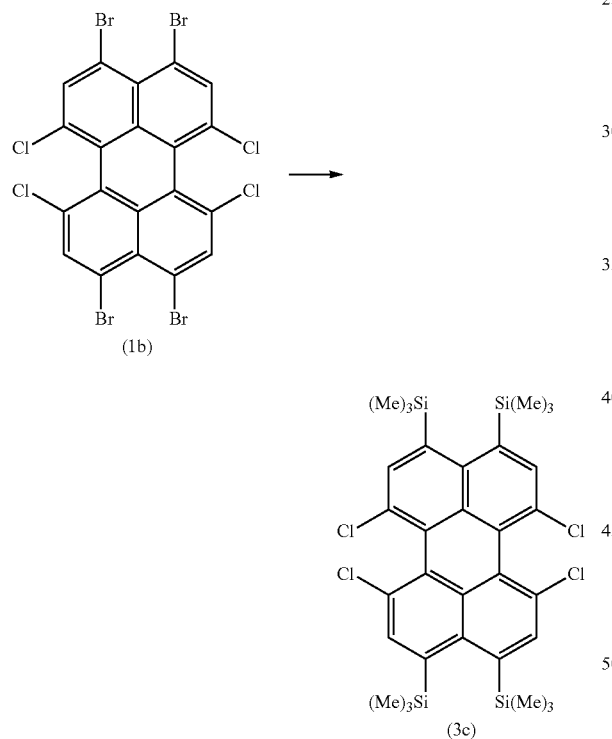

4.40 ml of solution of n-BuLi (1.6 M, 7 mmol) was added to a suspension of compound 1b (1 mmol, 706 mg) in 20 ml dry THF at −78° C. The reaction mixture was stirred at −78° C. for 1 h and TMSCl (0.90 ml, 7 mmol) was added dropwise to the solution. The mixture was allowed to warm gradually to room temperature and stirred additional 2 h. Methanol (1 ml) was added and the solvents were evaporated. The crude compound 3c was purified by column chromatography using hexane as eluent on silica and additional recrystallization from methanol. Yield 325 mg (48%). $^1$H-NMR ($\delta$(ppm), $CDCl_3$): 0.52 (s, 18H, $CH_3$); 0.54 (s, 18H, $CH_3$); 7.68 (s, 2H); 8.18 (s, 2H). $^{13}$C-NMR ($\delta$(ppm), $CD_2Cl_2$): 0.07 (6C, $CH_3$); 0.28 (6C, $CH_3$); 125.59 (2C); 125.84 (2C); 131.39 (2C); 132.67 (2C); 134.52 (2C); 134.93 (2C); 135.58 (2C); 138.28 (2C); 138.76 (2C); 140.26 (2C).

Example 12

Preparation of Compound 3d

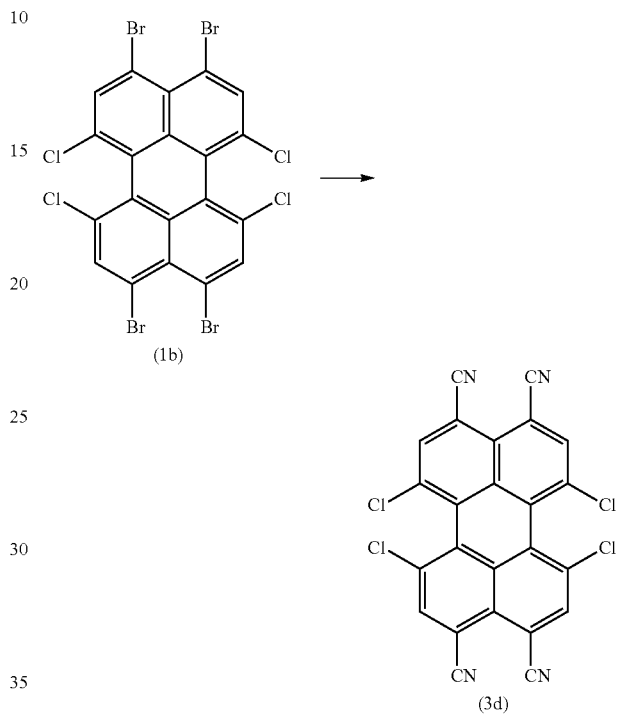

A suspension of compound 1b (2.11 g, 3.00 mmol) and CuCN (5.40 g, 60 mmol) in 50 ml DMF was stirred at 130° C. for 2 h. After cooling down to room temperature the reaction mixture was poured in water. The precipitate was filtered, dried and dissolved in 600 ml dichloromethane. 20 g of silica was added to the solution and evaporated to dryness. Crude compound 3d was purified by column chromatography using dichloromethane as eluent on silica. (1.03 g, 70%). FD-Mass: calc.: 490.13. found: 489.7. $^1$H-NMR ($\delta$(ppm), $C_2D_2Cl_4$): 8.21 (s, 4H, CH).

The invention claimed is:
1. A process for the preparation of compounds of formula

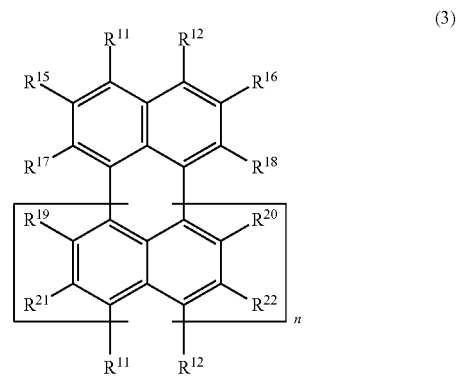

(3)

wherein
n is 0 or 1,
$R^{11}$ and $R^{12}$ are the same and are selected from the group consisting of CN, $OR^{300}$, $Si(R^{301})_3$, $NHR^{302}$, $NR^{303}R^{304}$, $SR^{305}$ and $R^{306}$,
wherein
$R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl or $C_{6-14}$-aryl,
wherein
$C_{1-20}$-alkyl, $C_{2-20}$-alkenyl and $C_{2-20}$-alkynyl may be substituted with one or more substituents selected from the group consisting of phenyl, $NR^{3000}R^{3001}$, $O-R^{3002}$ and $S-R^{3003}$ and
$C_{6-14}$-aryl may be substituted with one or more substituents selected from the group consisting of $C_{1-10}$-alkyl, $NR^{3004}R^{3005}$, $O-R^{3006}$ and $S-R^{3007}$,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{11}$ and $R^{12}$ together are selected from the group consisting of

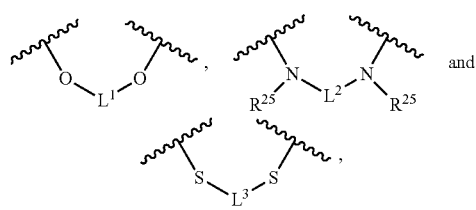

wherein
$L^1$ and $L^2$ are $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O-R^{3012}$ and $S-R^{3013}$, and
$C_{6-14}$-aryl may be substituted with one or more substituents selected from the group consisting of $C_{1-10}$-alkyl, $NR^{3014}R^{3015}$, $O-R^{3016}$ and $S-R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
$L^3$ is a direct bond, $C_{1-6}$-alkylene, $C_{6-14}$-arylene, or $C_{1-6}$-alkylene-$C_{6-14}$-arylene-$C_{1-6}$-alkylene,
and
$R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$,
wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O-R^{3022}$, $S-R^{3023}$, $NO_2$, CN and halogen,
$C_{6-14}$-aryl may be substituted with one or more substituents selected from the group consisting of $C_{1-10}$-alkyl, $NR^{3024}R^{3025}$, $O-R^{3026}$, $S-R^{3027}$, $NO_2$, CN and halogen,
wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl,
or
$R^{17}$ and $R^{19}$, respectively, $R^{18}$ and $R^{20}$ together are

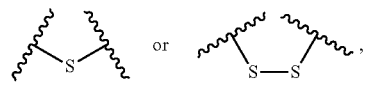

which process comprises the step of treating a compound of formula (2)

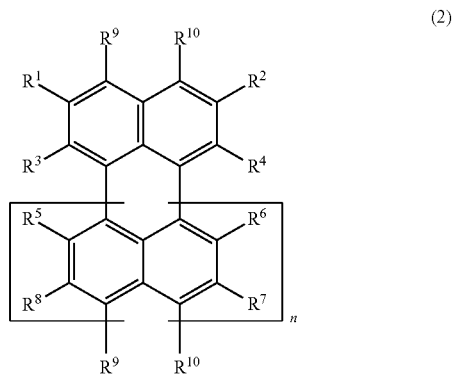

wherein
n has the meaning as depicted for formula (3),
$R^9$ and $R^{10}$ are the same or different and are COOH or $COOR^{200}$, wherein $R^{200}$ is $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2000}R^{2001}$, $O-R^{2002}$ and $S-R^{2003}$,
$C_{6-14}$-aryl may be substituted with one or more substituents selected from the group consisting of $C_{1-10}$-alkyl, $NR^{2004}R^{2005}$, $O-R^{2006}$ and $S-R^{2007}$,
wherein $R^{2000}$, $R^{2001}$, $R^{2002}$ and $R^{2003}$, $R^{2004}$, $R^{2005}$, $R^{2006}$ and $R^{2007}$ are the same or different and are $C_{1-10}$-alkyl or phenyl,
or
$R^9$ and $R^{10}$ together are

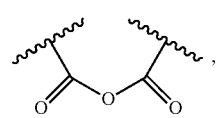 [SMILES: *C(=O)OC(*)=O]

and
$R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$ and $C(O)OR^{204}$, wherein $R^{200}$, $R^{201}$, $R^{202}$, $R^{203}$ and $R^{204}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O-R^{2012}$, $S-R^{2013}$, $NO_2$, CN and halogen,
$C_{6-14}$-aryl may be substituted with one or more substituents selected from the group consisting of $C_{1-10}$-alkyl, $NR^{2014}R^{2015}$, $O-R^{2016}$, $S-R^{2017}$, $NO_2$, CN and halogen,
wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl,
or
$R^3$ and $R^5$, respectively, $R^4$ and $R^6$ together are

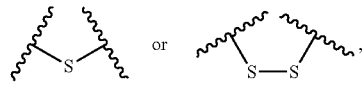

a) with MOH, wherein M is at least one alkali metal selected from the group consisting of Na, K and Li, $N(R^{400}R^{401}R^{402}R^{403})$, $P(R^{400}R^{401}R^{402}R^{403})$ or hexa($C_{1-10}$-alkyl)guanidinium,
wherein $R^{400}$, $R^{401}$, $R^{402}$ and $R^{403}$ are the same or different and are selected from the group consisting of H, $C_{1-20}$-alkyl, $C_{2-20}$-alkenyl, $C_{2-20}$-alkynyl, $C_{5-8}$-cycloalkyl and $C_{6-14}$-aryl,
wherein
$C_{1-20}$-alkyl, $C_{2-20}$-alkenyl, $C_{2-20}$-alkynyl and $C_{5-8}$-cycloalkyl may be substituted with phenyl,
$C_{6-14}$-aryl may be substituted with $C_{1-10}$-alkyl,
and
b) at least one X-donor selected from the group consisting of X—X, X-succinimide and N,N'-di-X-isocyanuric acid, wherein X is Cl, Br or I,
in order to obtain a compound of formula

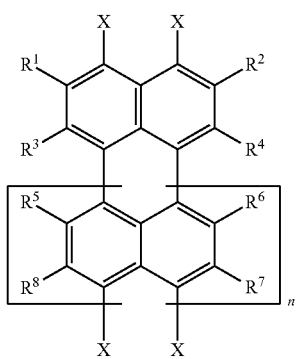

(1)

wherein
X has the meaning as depicted for the X-donor,
n has the meaning as depicted for formula (3),
and
$R^1$, $R^2$, $R^3$, $R^4$, $R^5$, $R^6$, $R^7$ and $R^8$ have the meaning as depicted for formula (2).

2. The process of claim 1, wherein $R^9$ and $R^{10}$ together are

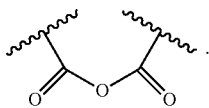

3. The process of claim 1, wherein n is 1.
4. The process of claim 1, wherein $R^1$, $R^2$, $R^3$, $R^4$, $R^5$, $R^6$, $R^7$ and $R^8$ are the same or different and are selected from the group consisting of H, Cl, Br, I, CN and $OR^{201}$,
wherein $R^{201}$ is $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O-R^{2012}$, $S-R^{2013}$, $NO_2$, CN and halogen,
$C_{6-14}$-aryl may be substituted with one or more substituents selected from the group consisting of $C_{1-10}$-alkyl, $NR^{2014}R^{2015}$, $O-R^{2016}$, $S-R^{2017}$, $NO_2$, CN and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl,
or
$R^3$ and $R^5$, respectively, $R^4$ and $R^6$ together are

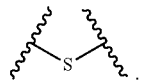

5. The process of claim 1, wherein $R^{15}$, $R^{16}$, $R^{17}$, $R^{18}$, $R^{19}$, $R^{20}$, $R^{21}$ and $R^{22}$ are the same or different and are selected from the group consisting of H, Cl, Br, I, CN and $OR^{311}$,
wherein $R^{311}$ is $C_{1-20}$-alkyl, $C_{2-20}$-alkenyl, $C_{2-20}$-alkynyl, $C_{5-8}$-cycloalkyl or $C_{6-14}$-aryl,
wherein
$C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O-R^{3022}$, $S-R^{3023}$, $NO_2$, CN and halogen,
$C_{6-14}$-aryl may be substituted with one or more substituents selected from the group consisting of $C_{1-10}$-alkyl, $NR^{3024}R^{3025}$, $O-R^{3026}$, $S-R^{3027}$, $NO_2$, CN and halogen,
wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl,
or
$R^{17}$ and $R^{19}$, respectively, $R^{18}$ and $R^{20}$ together are

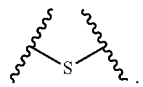

6. The process of claim 1, wherein $R^{11}$ and $R^{12}$ are the same and are selected from the group consisting of CN, $OR^{300}$ and $Si(R^{301})_3$,
wherein
$R^{300}$ and $R^{301}$ are $C_{1-20}$-alkyl, $C_{2-20}$-alkenyl, $C_{2-20}$-alkynyl or $C_{6-14}$-aryl, wherein C$_{1-20}$-alkyl, C$_{2-20}$-alkenyl and C$_{2-20}$-alkynyl may be substituted with one or more substituents selected from the group consisting of phenyl, NR$^{3000}$R$^{3001}$, O—R$^{3002}$ and S—R$^{3003}$ and C$_{6-14}$-aryl may be substituted with one or more substituents selected from the group consisting of C$_{1-10}$-alkyl, NR$^{3004}$R$^{3005}$, O—R$^{3006}$ and S—R$^{3007}$, wherein R$^{3000}$, R$^{3001}$, R$^{3002}$, R$^{3003}$, R$^{3004}$, R$^{3005}$, R$^{3006}$ and R$^{3007}$ are the same or different and are C$_{1-10}$-alkyl or phenyl, or R$^{11}$ and R$^{12}$ together are

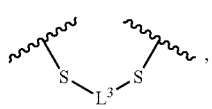

wherein

L$^3$ is a direct bond, C$_{1-6}$-alkylene, C$_{6-14}$-arylene, or C$_{1-6}$-alkylene-C$_{6-14}$-arylene-C$_{1-6}$-alkylene.

7. The process of claim 1, wherein R$^{11}$ and R$^{12}$ are the same and are selected from the group consisting of CN, OR$^{300}$ and Si(R$^{301}$)$_3$, wherein R$^{300}$ and R$^{301}$ are C$_{1-20}$-alkyl or C$_{6-14}$-aryl, wherein C$_{6-14}$-aryl may be substituted with one or more substituents selected from the group consisting of C$_{1-10}$-alkyl, NR$^{3004}$R$^{3005}$, O—R$^{3006}$ and S—R$^{3007}$, wherein R$^{3004}$, R$^{3005}$, R$^{3006}$ and R$^{3007}$ are the same or different and are C$_{1-10}$-alkyl or phenyl, or R$^{11}$ and R$^{12}$ together are

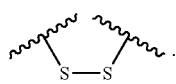

8. Compounds of formula

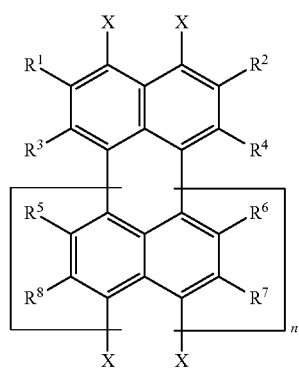

(1)

wherein

X is Cl, Br or I, n is 1, and

R$^1$, R$^2$, R$^3$, R$^4$, R$^5$, R$^6$, R$^7$ and R$^8$ are the same or different and are selected from the group consisting of H, F, Cl, Br, I, CN, R$^{200}$, OR$^{201}$, SR$^{202}$, OC(O)R$^{203}$ and C(O)OR$^{204}$, wherein R$^{200}$, R$^{201}$, R$^{202}$, R$^{203}$ and R$^{204}$ are C$_{1-20}$-alkyl, C$_{2-20}$-alkenyl, C$_{2-20}$-alkynyl, C$_{5-8}$-cycloalkyl or C$_{6-14}$-aryl, wherein C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{2010}$R$^{2011}$, O—R$^{2012}$, S—R$^{2013}$, NO$_2$, CN and halogen, C$_{6-14}$-aryl may be substituted with one or more substituents selected from the group consisting of C$_{1-10}$-alkyl, NR$^{2014}$R$^{2015}$, O—R$^{2016}$, S—R$^{2017}$, NO$_2$, CN and halogen, wherein R$^{2010}$, R$^{2011}$, R$^{2012}$, R$^{2013}$, R$^{2014}$R$^{2015}$, R$^{2016}$ and R$^{2017}$ are the same or different and are C$_{1-10}$-alkyl or phenyl, or R$^3$ and R$^5$, respectively, R$^4$ and R$^6$ together are

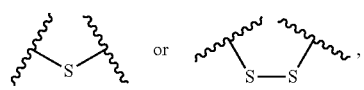

with the proviso that if n is 1 and X is Cl or Br, R$^1$, R$^2$, R$^3$, R$^4$, R$^5$, R$^6$, R$^7$ and R$^8$ are not H; and wherein R$^1$, R$^2$, R$^7$ and R$^8$ are H, and R$^3$, R$^4$, R$^5$ and R$^6$ are the same or different and are selected from the group consisting of F, Cl, Br, I, CN, R$^{200}$, OR$^{201}$, SR$^{202}$, OC(O)R$^{203}$ and C(O)OR$^{204}$, wherein R$^{200}$, R$^{201}$, R$^{202}$, R$^{203}$ and R$^{204}$ are C$_{1-20}$-alkyl, C$_{2-20}$-alkenyl, C$_{7-20}$-alkynyl, C$_{5-8}$-cycloalkyl or C$_{6-14}$-aryl, wherein C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{2010}$R$^{2011}$, O—R$^{2012}$, S—R$^{2013}$, NO$_2$, CN and halogen, C$_{6-14}$-aryl may be substituted with one or more substituents selected from the group consisting of C$_{1-10}$-alkyl, NR$^{2014}$R$^{2015}$, O—R$^{2016}$, S—R$^{2017}$, NO$_2$, CN and halogen, wherein R$^{2010}$, R$^{2011}$, R$^{2012}$, R$^{2013}$, R$^{2014}$, R$^{2015}$, R$^{2016}$ and R$^{2017}$ are the same or different and are C$_{1-10}$-alkyl or phenyl, or R$^3$ and R$^5$, respectively, R$^4$ and R$^6$ together are

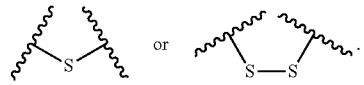

9. The compounds of claim 8, wherein R$^1$, R$^2$, R$^7$ and R$^8$ are H, and R$^3$, R$^4$, R$^5$ and R$^6$ are the same or different and are selected from the group consisting of Cl, Br, I, CN and OR$^{201}$, wherein R$^{201}$ is C$_{1-20}$-alkyl, C$_{2-20}$-alkenyl, C$_{2-20}$-alkynyl, C$_{5-8}$-cycloalkyl or C$_{6-14}$-aryl, wherein C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, $NR^{2010}R^{2011}$, $O\text{—}R^{2012}$, $S\text{—}R^{2013}$, $NO_2$, $CN$ and halogen, $C_{6-14}$-aryl may be substituted with one or more substituents selected from the group consisting of $C_{1-10}$-alkyl, $NR^{2014}R^{2015}$, $O\text{—}R^{2016}$, $S\text{—}R^{2017}$, $NO_2$, $CN$ and halogen, wherein $R^{2010}$, $R^{2011}$, $R^{2012}$, $R^{2013}$, $R^{2014}$, $R^{2015}$, $R^{2016}$ and $R^{2017}$ are the same or different and are $C_{1-10}$-alkyl or phenyl, or $R^3$ and $R^5$, respectively, $R^4$ and $R^6$ together are

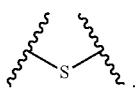

10. Compounds of formula

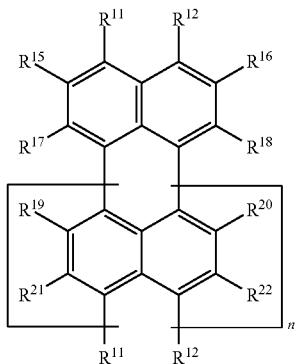

(3)

wherein n is 1, $R^{11}$ and $R^{12}$ are the same and are selected from the group consisting of $CN$, $OR^{300}$, $Si(R^{301})_3$, $NHR^{302}$, $NR^{303}R^{304}$, $SR^{305}$ and $R^{306}$ wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl or $C_{6-14}$-aryl, wherein $C_{1-20}$-alkyl, $C_{2-20}$-alkenyl, $C_{2-20}$-alkynyl may be substituted with one or more substituents selected from the group consisting of phenyl, $NR^{3000}R^{3001}$, $O\text{—}R^{3002}$ and $S\text{—}R^{3003}$ and $C_{6-14}$-aryl may be substituted with one or more substituents selected from the group consisting of $C_{1-10}$-alkyl, $NR^{3004}R^{3005}$, $O\text{—}R^{3006}$ and $S\text{—}R^{3007}$, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{11}$ and $R^{12}$ together are selected from the group consisting of

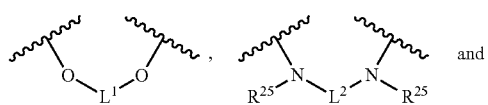 and

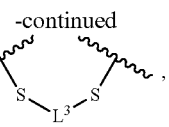

wherein $L^1$ and $L^2$ are $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O\text{—}R^{3012}$ and $S\text{—}R^{3013}$, and $C_{6-14}$-aryl may be substituted with one or more substituents selected from the group consisting of $C_{1-10}$-alkyl, $NR^{3014}R^{3015}$, $O\text{—}R^{3016}$ and $S\text{—}R^{3017}$, wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl, $L^3$ is a direct bond, $C_{1-6}$-alkylene, $C_{6-14}$-arylene, or $C_{1-6}$-alkylene-$C_{6-14}$-arylene-$C_{1-6}$-alkylene, and $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{310}$, $OR^{311}$, $SR^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3020}R^{3021}$, $O\text{—}R^{3022}$, $S\text{—}R^{3023}$, $NO_2$, $CN$ and halogen, $C_{6-14}$-aryl may be substituted with one or more substituents selected from the group consisting of $C_{1-10}$-alkyl, $NR^{3024}R^{3025}$, $O\text{—}R^{3026}$, $S\text{—}R^{3027}$, $NO_2$, $CN$ and halogen, wherein $R^{3020}$, $R^{3021}$, $R^{3022}$, $R^{3023}$, $R^{3024}$, $R^{3025}$, $R^{3026}$ and $R^{3027}$ are the same or different and are $C_{1-10}$-alkyl or phenyl, or $R^{17}$ and $R^{19}$, respectively, $R^{18}$ and $R^{20}$ together are

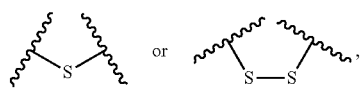

with the proviso that if $R^{11}$ and $R^{12}$ are both CN or phenyl, and $R^{15}$, $R^{16}$, $R^{18}$, $R^{19}$, $R^{20}$, $R^{21}$ and $R^{22}$ are H, then $R^{17}$ and $R^{20}$ are not Br; and wherein $R^{15}$, $R^{16}$, $R^{21}$ and $R^{22}$ are H, and $R^{17}$, $R^{18}$, $R^{19}$ and $R^{20}$, are the same or different and are selected from the group consisting of F, Cl, Br, I, CN, $R^{310}$, $OR^{311}$, $R^{312}$, $OC(O)R^{313}$ and $C(O)OR^{314}$, wherein $R^{310}$, $R^{311}$, $R^{312}$, $R^{313}$ and $R^{314}$ are $C_{1-20}$-alkyl, $C_{2-20}$-alkenyl, $C_{2-20}$-alkynyl, $C_{5-8}$-cycloalkyl or $C_{6-14}$-aryl, wherein C$_{1-20}$-alkyl, C$_{7-20}$-alkenyl, C$_{2-20}$-alkynyl and C$_{5-8}$-cycloalkyl may be substituted with one or more substituents selected from the group consisting of phenyl, NR$^{3020}$R$^{3021}$, O—R$^{3022}$, S—R$^{3023}$, NO$_2$, CN and halogen, C$_{6-14}$-aryl may be substituted with one or more substituents selected from the group consisting of C$_{1-10}$-alkyl, NR$^{3024}$R$^{3025}$, O—R$^{3026}$, S—R$^{3027}$, NO$_2$, CN and halogen, wherein R$^{3020}$, R$^{3021}$, R$^{3022}$, R$^{3023}$, R$^{3024}$, R$^{3025}$, R$^{3026}$ and R$^{3027}$ are the same or different and are C$_{1-10}$-alkyl or phenyl, or R$^{17}$ and R$^{19}$, respectively, R$^{18}$ and R$^{20}$ together are

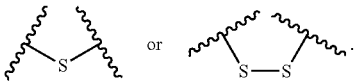

11. The compounds of claim 10, wherein R$^{11}$ and R$^{12}$ are the same and are selected from the group consisting of CN, OR$^{300}$ and Si(R$^{301}$)$_3$, wherein R$^{300}$ and R$^{301}$ are C$_{1-20}$-alkyl, C$_{2-20}$-alkenyl, C$_{2-20}$-alkynyl or C$_{6-14}$-aryl, wherein C$_{1-20}$-alkyl, C$_{2-20}$-alkenyl and C$_{2-20}$-alkynyl may be substituted with one or more substituents selected from the group consisting of phenyl, NR$^{3000}$R$^{3001}$, O—R$^{3002}$ and S—R$^{3003}$ and C$_{6-14}$-aryl may be substituted with one or more substituents selected from the group consisting of C$_{1-10}$-alkyl, NR$^{3004}$R$^{3005}$, O—R$^{3006}$ and S—R$^{3007}$, wherein R$^{3000}$, R$^{3001}$, R$^{3002}$, R$^{3003}$, R$^{3004}$, R$^{3005}$, R$^{3006}$ and R$^{3007}$ are the same or different and are C$_{1-10}$-alkyl or phenyl, or R$^{11}$ and R$^{12}$ together are

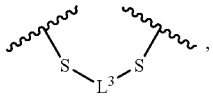

wherein

L$^3$ is a direct bond, C$_{1-6}$-alkylene, C$_{6-14}$-arylene, or C$_{1-6}$-alkylene-C$_{6-14}$-arylene-C$_{1-6}$-alkylene.

12. The compounds of claim 10, wherein R$^{11}$ and R$^{12}$ together are

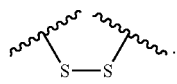 [SMILES: *SS*]

* * * * *